(12) United States Patent
Castañeda et al.

(10) Patent No.: US 6,464,690 B1
(45) Date of Patent: *Oct. 15, 2002

(54) PORT OFF-PUMP BEATING HEART CORONARY ARTERY BYPASS HEART STABILIZATION SYSTEM

(75) Inventors: Javier E. Castañeda, Miami; Jose Luis Francese, Springs; Matthew A. Palmer, Miami, all of FL (US); Ralph de la Torre, Charlestown, MA (US)

(73) Assignee: Popcab, LLC, Miami, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 36 days.

(21) Appl. No.: 09/686,530

(22) Filed: Oct. 11, 2000

(51) Int. Cl.⁷ .............................................. A61B 17/00
(52) U.S. Cl. ............................ 606/1; 600/215; 600/235
(58) Field of Search ................................ 600/201, 208, 600/210, 215, 235, 102; 606/1, 108, 130; 604/174, 164.04, 513, 533, 539

(56) References Cited

U.S. PATENT DOCUMENTS

| | | | |
|---|---|---|---|
| 5,104,383 A | 4/1992 | Shichman | 604/167 |
| 5,147,316 A | 9/1992 | Castillenti | 604/164 |
| 5,176,648 A | 1/1993 | Holmes et al. | 604/164 |
| 5,364,367 A | 11/1994 | Banks et al. | 604/174 |
| 5,374,277 A | 12/1994 | Hassler | 606/207 |

(List continued on next page.)

FOREIGN PATENT DOCUMENTS

| | | |
|---|---|---|
| CA | 2216893 | 7/1997 |
| DE | 29707567 U1 | 7/1997 |
| EP | 0336 526 A1 | 10/1989 |
| EP | 0356410 A1 | 2/1990 |
| EP | 0630629 A1 | 12/1994 |

(List continued on next page.)

OTHER PUBLICATIONS

Pilling Surgical Instruments 1993 catalogue, p. 304, designs for Miscellaneous Heart Instruments.
Article entitled "Left Anterior Descending Coronary Artery Grafting via Left Anterior Small Thoracotomy without Cardiopulmonary Bypass" by Calafiore et al., in the 1996 Journal, The Society of Thoracic Surgeons, pp. 1658–1665.

(List continued on next page.)

*Primary Examiner*—Linda C. M. Dvorak
*Assistant Examiner*—Jocelyn Ram
(74) *Attorney, Agent, or Firm*—David P Gordon; David S Jacobson; Thomas A Gallagher

(57) ABSTRACT

A heart stabilizer includes a shaft and two articulating arms coupled to a distal end of the shaft. At the end of each arm is a rotatable foot adapted to be angled relative to the heart wall contour and apply pressure against the wall of the heart to effectively eliminate motion of the heart wall between the feet. The stabilizer is adapted to provide a stabilized area sufficiently large to allow an accurate anastomosis to be performed. According to preferred aspects of the invention, the stabilizer is particularly adapted to be collapsible (foldable) to be inserted through the port device and locked longitudinally relative thereto. The stabilizer is also preferably adapted to be automatically deployed into its final configuration by release of a lock actuated at a proximal portion of stabilizer extending outside the port. In addition, the stabilizer is adapted to automatically fold when being pulled back through the port. According to various embodiments of the heart stabilizer, the feet of the stabilizer may be further adapted to facilitate immobilization of the heart wall between the feet.

32 Claims, 26 Drawing Sheets

U.S. PATENT DOCUMENTS

| | | | |
|---|---|---|---|
| 5,375,588 A | 12/1994 | Yoon | 128/4 |
| 5,389,081 A | 2/1995 | Castro | 604/167 |
| 5,391,156 A | 2/1995 | Hildwein et al. | 604/174 |
| 5,407,427 A | 4/1995 | Zhu et al. | 604/26 |
| 5,445,615 A | 8/1995 | Yoon | 604/96 |
| 5,452,733 A | 9/1995 | Sterman et al. | 128/898 |
| 5,472,429 A | 12/1995 | Yoon | 604/178 |
| 5,476,479 A | 12/1995 | Green et al. | 606/205 |
| 5,490,843 A | 2/1996 | Hildewein | 604/164 |
| 5,540,648 A | 7/1996 | Yoon | 600/114 |
| 5,545,179 A | 8/1996 | Williamson, IV | 606/213 |
| 5,571,072 A | 11/1996 | Kronner | 600/102 |
| 5,582,577 A | 12/1996 | Lund et al. | 600/204 |
| 5,613,937 A | 3/1997 | Garrison et al. | 600/201 |
| 5,637,097 A | 6/1997 | Yoon | 604/174 |
| 5,653,718 A | 8/1997 | Yoon | 606/148 |
| 5,685,857 A | 11/1997 | Negus | 604/170 |
| 5,688,247 A | 11/1997 | Haindl | 604/175 |
| 5,707,362 A | 1/1998 | Yoon | 604/164 |
| 5,713,869 A | 2/1998 | Morejon | 604/174 |
| 5,725,553 A | 3/1998 | Moenning | 606/213 |
| 5,735,290 A | 4/1998 | Sterman et al. | 128/898 |
| 5,749,892 A | 5/1998 | Vierra et al. | 600/204 |
| 5,782,813 A | 7/1998 | Yoon | 604/174 |
| 5,799,661 A | 9/1998 | Boyd et al. | 128/898 |
| 5,807,243 A | 9/1998 | Vienna et al. | 600/204 |
| 5,817,062 A | 10/1998 | Flom | 604/174 |
| 5,820,555 A | 10/1998 | Watkins, III | 600/204 |
| 5,823,946 A | 10/1998 | Chin | 600/604 |
| 5,836,913 A | 11/1998 | Orth et al. | 604/107 |
| 5,865,730 A | 2/1999 | Fox et al. | 600/228 |
| 5,865,809 A | 2/1999 | Moenning et al. | 604/174 |
| 5,865,817 A | 2/1999 | Moenning et al. | 604/283 |
| 5,875,782 A * | 3/1999 | Ferrari et al. | 128/898 |
| 5,894,843 A | 4/1999 | Benetti et al. | 128/898 |
| 5,976,080 A | 11/1999 | Farascioni | 600/213 |
| 5,980,455 A | 11/1999 | Daniel et al. | 600/235 |
| 6,007,486 A | 12/1999 | Hunt et al. | 600/205 |
| 6,015,378 A | 1/2000 | Borst et al. | 600/37 |
| 6,017,304 A | 1/2000 | Vierra et al. | 600/204 |
| 6,019,722 A | 2/2000 | Spence et al. | 600/210 |
| 6,027,476 A | 2/2000 | Sterman et al. | 604/966 |
| 6,033,362 A | 3/2000 | Cohn | 600/213 |
| 6,033,426 A | 3/2000 | Kaji | 606/213 |
| 6,036,641 A | 3/2000 | Taylor et al. | 600/231 |
| 6,039,725 A | 3/2000 | Moenning et al. | 606/1 |
| 6,045,536 A | 4/2000 | Meier et al. | 604/174 |
| 6,050,266 A * | 4/2000 | Benetti et al. | 128/898 |
| 6,056,689 A | 5/2000 | Lenox et al. | 600/217 |
| 6,056,766 A | 5/2000 | Thompson et al. | 606/185 |
| 6,063,021 A | 5/2000 | Hossain et al. | 600/37 |
| 6,110,187 A | 8/2000 | Donlon | 606/151 |
| 6,113,534 A | 9/2000 | Koros et al. | 600/213 |
| 6,132,370 A * | 10/2000 | Furnish et al. | 600/235 |
| 6,139,492 A | 10/2000 | Vierra et al. | 600/204 |
| 6,193,652 B1 * | 2/2001 | Berky et al. | 600/205 |
| 6,254,535 B1 * | 7/2001 | Hu et al. | 600/232 |
| 6,283,912 B1 * | 9/2001 | Rogers et al. | 600/37 |
| 6,290,644 B1 * | 9/2001 | Green et al. | 600/235 |
| 6,315,717 B1 * | 11/2001 | Benetti et al. | 600/210 |
| 2001/0023311 A1 * | 9/2001 | Snow | 600/37 |

FOREIGN PATENT DOCUMENTS

| | | |
|---|---|---|
| EP | 0791330 A2 | 8/1997 |
| EP | 0820721 A1 | 1/1998 |
| FR | 1019217 | 1/1956 |
| WO | WO87/04081 | 7/1987 |
| WO | WO94/14383 | 7/1994 |
| WO | WO95/15715 | 6/1995 |
| WO | WO95/17127 | 6/1995 |
| WO | WO 96/04854 | 2/1996 |
| WO | WO97/10753 | 3/1997 |
| WO | WO97/20524 | 6/1997 |
| WO | WO97/27807 | 8/1997 |
| WO | WO98/25549 | 6/1998 |
| WO | WO99/11201 | 3/1999 |

OTHER PUBLICATIONS

Article entitled "Coronary Artery Bypass without Cardiopulmonary Bypass" by Pfister et al, in the 1992 Journal, The Society of Thoracic Surgeons, pp. 1085–1092.

Article entitled "Snaring of the Target Vessel in Less Invasive Bypass Operations does not cause Endothelial Dysfunction", by Perrault et al., in the 1997 Journal, The Society of Thoracic Surgeons, pp. 751–755.

Article entitled "Triple Coronary Artery Revascularization on the Stabilized Beating Heart: Initial Experience", by Cartier et al., from the Department of Cardiovascular Surgery and the Dept. of Anesthesiology, Montreal Heart Institute, Sep. 19, 1997, pp. 283–288.

Article entitled "Direct Myocardial Revascularization by Saphenous Vein Graft" by Favaloro et al. in the Aug. 1970, vol. 10, Journal of The Society of Thoracic Surgeons, pp. 97–111.

Editorial entitled "Coronary Surgery without Cardiopulmonary bypass", in British Heart Journal, 1995;73:pp. 203–205.

Article entitled "The Cardiac Rag– simple exposure of the heart" by Badellino et al., vol. 15, No. 2, 1988 in the Texas Heart Institute Journal, pp. 134–135.

Letter to the Editor in Archives of Surgery, vol. 115, No. 9, Sep. 1980, on "New Use for an Old Clamp", 4 pages.

J Cardiovasc Surgery,30, 1989, pp. 996–997, Technical Comments article entitled"Internal mammary artery dissection: A three dimensional sternal retractor" by Roux et al.

Article entitled "Off–Bypass Coronary Grafting via Minithoracotomy using Mechanical Epicardial Stabilization", by Cremer et al., in the 1997 Journal, The Society of Thoracic Surgeons, pp. 579–583.

Article entitled "Single coronary bypass grafting– a comparison between minimally invasive "off pump" techniques and conventional procedures", by Bonatti et al., in the European Journal of Cardio–thoracic Surgery 17 (Suppl 1), 1998, pp. S7–S12.

Article entitled "Less Invasive Coronary Surgery: Consensus from the Oxford Meeting", by Westaby et al., in the 1996 Journal, The Society of Thoracic Surgeons, pp. 924–931.

Article entitled "Mini–Sternotomy for Coronary Artery Bypass Grafting", by Arom et al., in the 1996 Journal, The Society of Thoracic Surgeons, pp. 1271–1272.

Article entitled "Limited Access Myocardial Revascularization" by Cooley, in the Texas Heart Institute Journal, vol. 23, No. 2, 1996, pp. 81–84.

Letter to the Editor on Mini–Sternotomy for Coronary Artery Bypass Grafting by A. Cohen et al., 1996, pp. 1884–1885, Journal, The Society of Thoracic Surgeons.

Article entitled "Fabric Heart Retractor for Coronary Artery Bypass Operations" by Kazama et al. in the 1993 Journal, The Society of Thoracic Surgeons, pp. 1582–1583.

Article entitled "Minimally Invasive Coronary Artery Bypass Grafting" by Calafiore et al. in the 1996 Journal, The Society of Thoracic Surgeons, pp. 1545–1548.

Article entitled "Improved Visualization of the Internal Mammary Artery with a New Retractor System" by Pittman et al. in the 1989 Journal, The Society of Thoracic Surgeons, pp. 869–879.

Article entitled "A Modified Sternal Retractor" by Ancalmo et al. from the Dept. of Surgery, Alton Ochsner Medical Foundation and Ochsner Clinic, New Orleans, LA, Aug., 8, 1975., p. 174.

Article entitled "A Versatile Retractor For Use In Harvesting The Internal Mammary Artery And Performing Standard Cardiac Operations" by Phillips et al., in the J Thoracic Cardiovasc Surg 1989, vol. 97, pp. 633–635.

Article entitled "Surgical Management of Diseased Intracavitary Coronary Arteries" by Ochsner et al. in The Annals of Thoracic Surgery, vol. 38, No. 4, Oct. 1984, pp. 356–362.

Article entitled "Technique of internal mammary–coronary artery anastomosis" by Green, in the Journal of Thoracic Surgery, vol. 78, 1979, pp. 455–459.

Article entitled "Graduated probes for coronary bypass surgery" by Parsonner et al., in the Journal of Thoracic and Cardiovascular Surgery, vol. 68, No. 3, Sep. 1974, pp. 424–427.

Article entitled "A Modified Sternal Retractor for Exposure of the Internal Mammary Artery" by McKeown et al., in the Society of Thoracic Surgeons, 1980, p. 619.

Article entitled "A New Concept in Sternal Retraction: Application for Internal Mammary Artery Dissection and Valve Replacement Surgery" by Chaux et al., in the Annals of Thoracic Surgery, vol. 42, Oct. 1986, pp. 473–474.

Article entitled "Cardiac Retractor for Coronary Bypass Operations" by Rousou et al., in The Society of Thoracic Surgeons, 1991, pp. 877–878.

Article entitled A New Retractor to Aid in Coronary Artery Surgery: by DelRossi et al., in the in the Annals of Thoracic Surgery, vol. 36, No. 1, Jul. 1983.

Article entitled "New Helper Instrument in Cardiac Surgery" by Roux et al., in the Society of Thoracic Surgeons, 1989, pp. 505–596.

Article entitled "Aortic Spoon–Jaw Clamp for Aorto–Saphenous Vein Anastomosis" by Robicsek, in the Journal of Card Surg, 1995; vol. 10, pp. 583–585.

Article entitled "Techniques of dissecting the internal mammary after using the Moussalli bar" by Hasan et al. , the European J Cardio–thorac Surg, 1990, vol. 4, pp. 571–572.

Article entitled "Self–Retaining Epicardial Retractor For Aortocoronary Bypass Surgery" by Parsonnet et al., in the Journal of Thoracic and Cardiovascular Surgery, 1979, pp. 629–630.

Article entitled Coronary Artery bypass Grafting without Cardiopulmonary Bypass and Without Interruption of Native Coronary Flow Using a Novel Anastomosis Site Restraining Device ("Octopus"), by Borst et al., JACC, vol. 27 No. 6, May 1996, pp. 1356–1364.

Article entitled "A New Internal Mammary Artery Retractor" by Bugge, in the Thorac.cardiovasc.Surgeon, vol. 38, 1990, pp. 316–317.

Article entitled "A Simple, Inexpensive Method of Heart Retraction During Coronary Artery Bypass Surgery" by Angelini, in the Ann Thorac Surg, vol. 46, pp. 246–247, Aug. 1988.

Article entitled A New Device for Exposing the Circumflex Coronary Artery: by Matsuura et al., in the Society of Thoracic Surgeons, 1995, pp. 1249–1250.

Article entitled "Application of a Special vasal devaricator during coronary surgery" by Vigano, in the Minerva Cardioangiologica, Jul. 1975, pp. 370–371.

Translation of "Heart Retractor for Use in Anastomosis in Coronary Artery By–pass Surgery" by Eguchi, from the Japanese Journal of Thoracic Surgery, vol. 40, No. 1, 1987, 4 pages.

Japanese article (title translated) on "A Special Retractor for Stabilizing the Heart During Circumflex Coronary Grafting"by Eguchi, 1987, 2 pages.

Article entitled "Revascularization of the Circumflex Coronary Artery—A new Instrument and a Technical Method– " by Murata, in the Japanese Journal of Thoracic Surgery, 1989, vol. 42, No. 2, 6 pages.

* cited by examiner

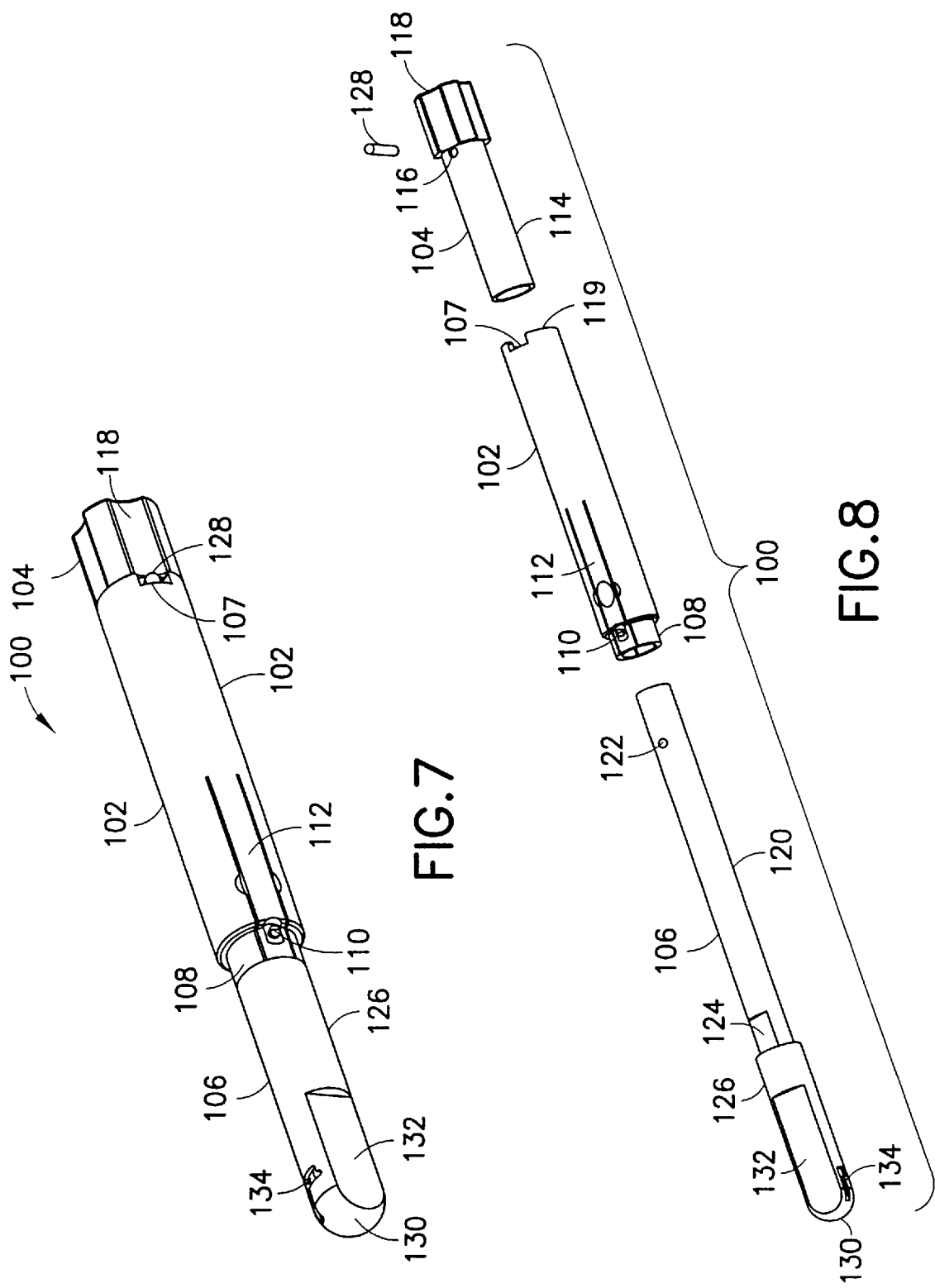

PORT OFF-PUMP BEATING HEART CORONARY ARTERY BYPASS HEART STABILIZATION SYSTEM

BACKGROUND OF THE INVENTION

1. Field of the Invention

This invention relates broadly to surgical instruments and systems. More particularly, this invention relates to ports for surgical instruments and systems for performing coronary artery bypass surgery.

2. State of the Art

Substantially all coronary artery bypass (CAB) procedures are performed via an open chest method. In the procedure, the chest is opened through an incision in the middle of the chest, called a sternotomy, and the ribs are retracted and held stably open with a retractor. This provides a sufficient amount of access to the heart. The heart is then arrested and the blood flow is rerouted through a heart-lung machine. The bypass procedure is then performed, and once complete, the heart is then restarted and blood is permitted to flow through the "bypass". While this procedure is the norm, it is far from desirable. First, arresting the heart is a dangerous procedure and can lead to serious complications and even death. Second; the procedure requires a sternotomy, which is painful and traumatic. Because of this incision the recovery time is relatively long and the patient is left with a permanent large scar.

More recently, some surgeons have performed coronary artery bypass surgery on a beating heart. The chest is opened via a sternotomy and retracted. Using a device called a heart stabilizer, the surgical site on the heart is essentially immobilized for suturing. The heart stabilizer is typically anchored to the retractors which are in turn anchored to the walls of the chest at the site of the incision. Direct access to the surgical site as well as immobilization of the surgical site are key to the surgery. These factors allow the surgeon to perform a suture or other operation with precision. While the methodology is effective and eliminates the potential complications of arresting the heart, the drawbacks associated with the sternotomy remain.

It has recently been proposed by others to perform a closed chest bypass procedure on the beating heart. However, the proposal has not been followed by any concrete directions on how to satisfactorily perform the procedure. In addition, the inventors of the present application have recognized that the closed chest procedure has a number of hurdles to overcome. First, it is necessary to stabilize the heart such that the location requiring the bypass does not significantly move during the procedure. Second, while open chest procedure are accompanied by a retractor and instrument supporting framework, in a closed chest procedure, there is no such framework for holding the instruments required for the procedure. In addition, there is no suitable stable port device adapted to securely support instruments passing therethrough.

SUMMARY OF THE INVENTION

It is therefore an object of the invention to provide a less traumatic instrument access to the surgical site.

It is another object of the invention to provide a port device which is easy to insert into the body.

It is a further object of the invention to provide a port device with a high degree of stability.

It is an additional object of the invention to provide a heart stabilizer which can be inserted through the port device and which is adapted to stabilize a portion of a beating heart such that coronary artery bypass surgery can be performed on the portion of the heart.

It is also an additional object of the invention to provide a heart stabilizer which can be manipulated via a proximal handle external of the port device.

It is yet another object of the invention to provide a system of components which cohesively operates together to facilitate port off-pump coronary artery bypass surgery on a beating heart.

It is yet a further object of the invention to provide a method of performing port off-pump coronary artery bypass surgery on a beating heart.

In accord with these objects, which will be discussed in detail below, a system for performing port off-pump beating heart coronary artery bypass (POPCAB) surgery is provided. The system includes a port device and a heart stabilizer.

The port device is insertable between the ribs of the patient and functions as an entry way for each instrument necessary for the procedure, e.g., optics, graspers, needle holders, suction/irrigation tubes, stabilizers. According to a preferred aspect of the invention, the port device includes a tubular body having proximal and distal portions and intended to be inserted through a pair of ribs in a chest wall of a patient. The proximal portion of the tubular body includes a plurality of thread grooves extending at least partially about a circumference of the body as well as a means to permit the heart stabilizer or another device to be releasably secured to the port. The distal portion of the tubular body is coupled to a swivel adapted to be moved between a first orientation in which the swivel extends in substantially a same direction as the body, and a second orientation at an angle relative to, and preferably substantially perpendicular to, the first orientation.

According to first and second embodiments of the port device, a washer is positioned on the body between the swivel and the proximal portion of the body, and a locknut is threadably engaged in the thread grooves. When the tubular body is inserted between two ribs in the chest wall of the patient, the swivel is then opened into the second orientation and the washer is moved along the body to position the chest wall between the swivel and the washer. The locknut is then tightened about the body to clamp the washer against the chest wall and stably secure the tubular body within the chest wall.

According to a third embodiment of the port device, a platform movable along the length of the port body includes adjustable legs and feet. The legs are adjusted such that the feet contact the chest wall and clamp the chest wall between the feet-and the swivel. In addition, the legs may be adjusted to provide the body in a desired angle relative to the chest wall.

According to various aspects of the several embodiments of the port, the port may include a thread system adapted to permit quick locking of the locknut against the washer or the platform along the body, one or two swivels, and/or a ball joint permitting angular orientation of the port to permit the port to be directed toward a desired location such as the surgical site. In addition, the swivel or swivels may be spring biased to move from the first orientation to the second orientation, or an introducer device may be provided to mechanically move the swivel or swivels between the first and second orientations.

The heart stabilizer preferably includes a shaft and two jointed arms coupled to a distal end of the shaft. At the end of each arm is a rotatable foot adapted to be angled relative to the heart wall contour and apply pressure against the wall of the heart to effectively eliminate motion of the heart wall between the feet. The stabilizer is adapted to provide a stabilized area sufficiently large to allow an accurate anastomosis to be performed. According to preferred aspects of the invention, the stabilizer is particularly adapted to be collapsible (foldable) to be inserted through the port device and locked longitudinally relative thereto. The stabilizer is also preferably adapted to be automatically deployed into its final configuration by release of a lock actuated at a proximal portion of the stabilizer extending outside the port. In addition, the stabilizer is adapted to automatically fold when being pulled back through the port.

According to various embodiments of the heart stabilizer, the feet of the stabilizer may be further adapted to facilitate immobilization of the heart wall between the feet. In addition to compressive forces, the feet may apply suction, chemical agents, electrical current, or thermal cooling to enhance the heart wall immobilization.

The port device and heart stabilizer together define a surgical system for performing port off-pump beating heart coronary artery bypass (POPCAB) surgery. According to a preferred method, two port devices are stably positioned in the chest wall and directed as necessary for operation on the heart wall. A heart stabilizer is coupled to one port, and operated to apply a compressive force against the heart wall surrounding a location of the required bypass such that the location is substantially immobilized. A surgical instrument, e.g., a scalpel or needle holder, is passed through the other port and operated to perform at least a portion of the procedure. If other instruments are required, the instrument within the port may be removed therefrom and other instruments may be extended therethrough. Alternatively, ports may be provided for each instrument. Once the bypass procedure is complete, the instrument is removed from the locus of the surgery and the associated port, and the heart stabilizer is also removed through its port. Then, the clamping forces on the ports are loosened, the swivels located in the first configuration, and the ports are withdrawn from the chest wall. Finally, the incision in which the ports were located are closed. This method eliminates the need for many open heart procedures, as well as the need to stop the heart.

Additional objects and advantages of the invention will become apparent to those skilled in the art upon reference to the detailed description taken in conjunction with the provided figures.

BRIEF DESCRIPTION OF THE DRAWINGS

FIG. 7 is a front perspective view of an introducer according to the invention;

FIG. 8 is an exploded perspective view of the introducer of FIG. 7;

DETAILED DESCRIPTION OF THE PREFERRED EMBODIMENTS

According to the invention, a system is provided for performing port off-pump beating heart coronary artery bypass (POPCAB) surgery. The system includes a port device and a heart stabilizer.

Figure 1:
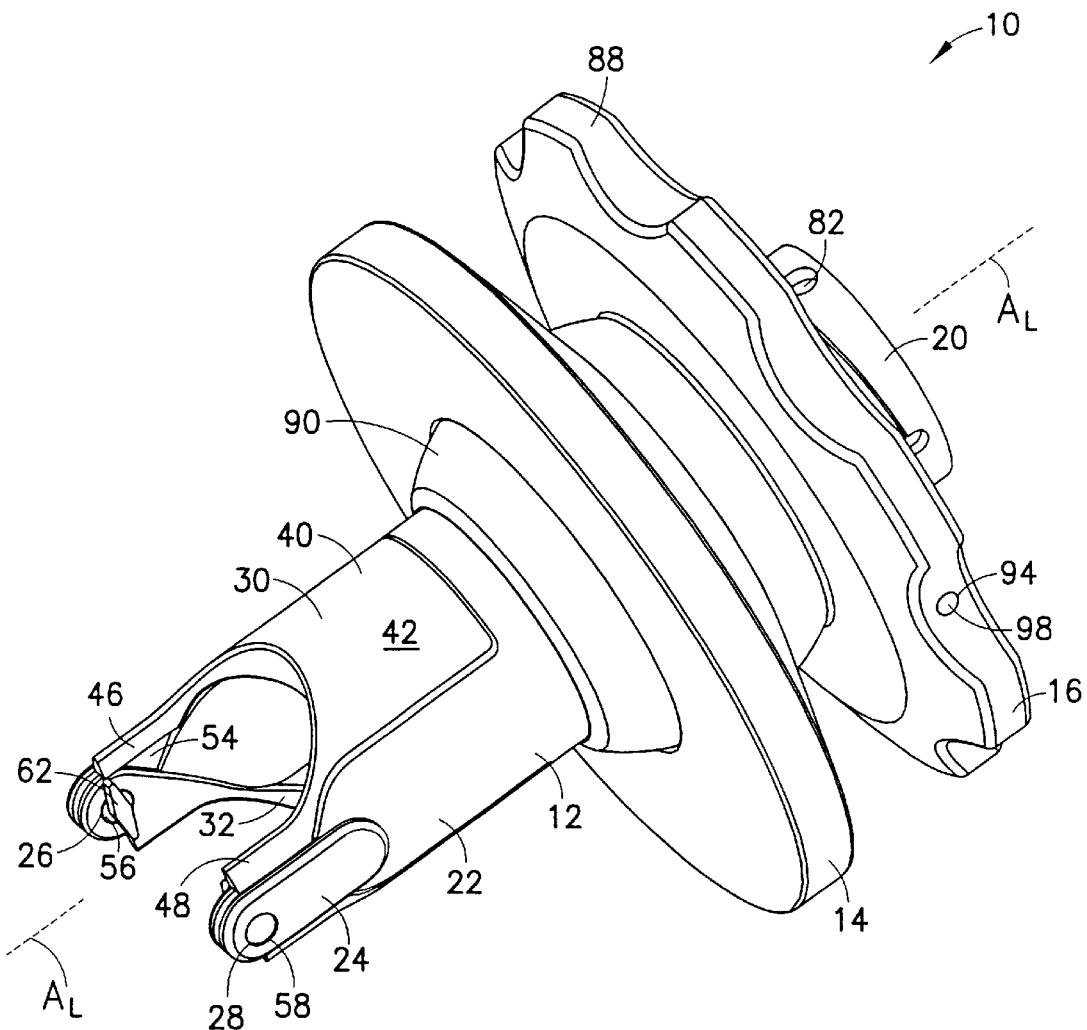
FIG. 1 is a bottom perspective view of a first embodiment of a port device according to the invention, shown with the swivels in a closed configuration.

Turning now to FIG. 1, a first embodiment of the port device 10 includes a tubular body 12, a washer 14 slidably mounted on the tubular body and a locknut 16 threadably coupled to the body 12 proximal of the washer 14. The tubular body 12 includes a proximal portion 20 and a distal portion 22. The distal portion 22 includes a clevis 24 defining two coaxial pivot bores 26, 28, and a pair of clamping swivels 30, 32 are rotatably coupled to the clevis 24 at the pivot bores 26, 28.

Figure 2:
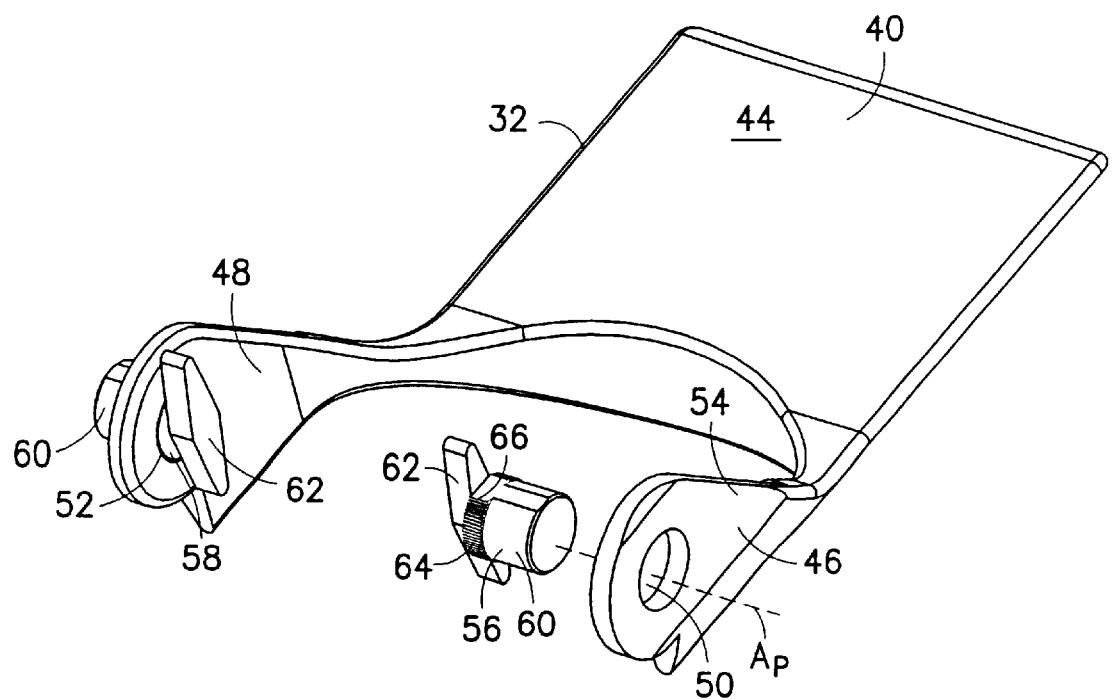
FIG. 2 is a partially disassembled top perspective view of a swivel and pivot axles according to the first embodiment of a port device according to the invention.
Figure 3:
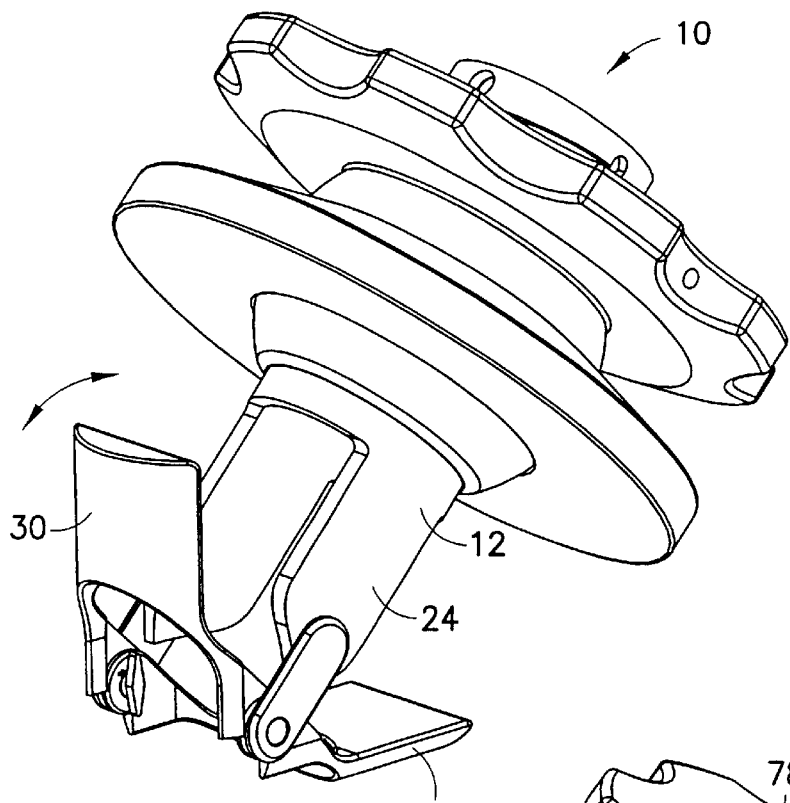
FIG. 3 is a bottom perspective view of the first embodiment of the port device according to the invention, shown with the swivels in a partly open configuration.
Figure 4:
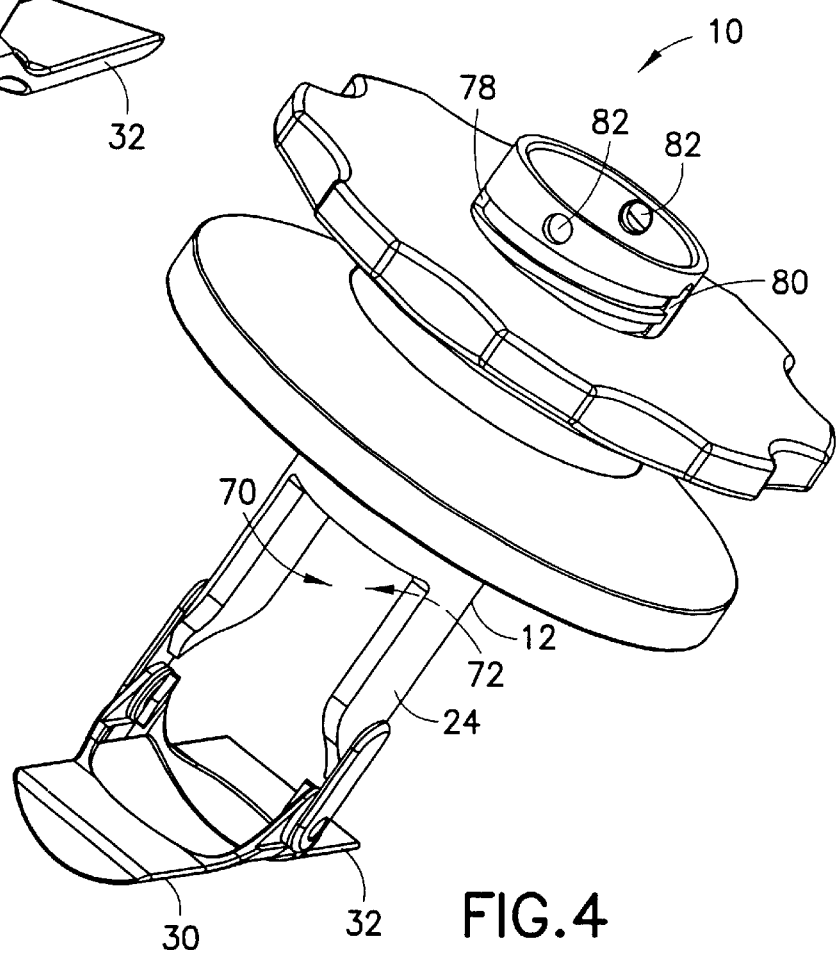
FIG. 4 is a top perspective view of the first embodiment of the port device according to the invention, shown with the swivels in an open configuration.

Referring to FIGS. 1 and 2 and with reference to swivel 32, each swivel includes a wing portion 40 with a preferably curved outer surface 42 and a preferably substantially planar inner contact surface 44, and two arms 46, 48 each including an axle bore 50, 52. One arm 46 of each swivel includes an inner recess 54 adapted to permit interleaving of the swivels about the clevis 24. Each arm 46, 48 of the swivel is coupled to the tubular body 12 with an axle member 56, 58 which extends through a respective axle bore 50, 52 and pivot bore 26, 28, and defines a pivot axis $A_p$. With reference to axle member 56, each axle member includes a relatively cylindrical first portion 60, an elongate trapezoidal-shaped lever 62, and an interference portion 64 between the first portion and lever portion. The interference portion 64 is slightly larger in diameter than the first portion 62 and includes knurls 66 or other gripping structure. The interference portion 64 of axle member 56 engages arm 46 about a respective axle bore, and the first portion 60 extends into the clevis bore 26, in which it is freely rotatable, while the interference portion 64 of axle member 58 engages arm 48 about a respective axle bore. As such, each axle member 56, 58 is fixedly attached to only one of the swivels and the swivel pivots about it. Then, as each swivels rotates about the clevis, a respective lever is also rotated and, similarly, rotation of the individual levers results in independent rotation of the swivels. The swivels 30, 32 are rotatable from a closed orientation (FIG. 1) in which the swivels extend substantially parallel to the body 12 through intermediate orientations (e.g., FIG. 3), and into a open orientation in which the swivels 30, 32 extend preferably perpendicular to the first orientation (FIG. 4). When in the first orientation, the swivels 30, 32 preferably complete the openings 72, 74 (FIG. 4) defined by the clevis 24, and the curvature of the outer surfaces 42 of the swivels provide the outer surface of the distal portion 22 with a substantially smooth surface. In addition, in the first orientation, the levers 62 are preferably oriented transverse the longitudinal axis $A_L$ of the body 12.

Figure 5:
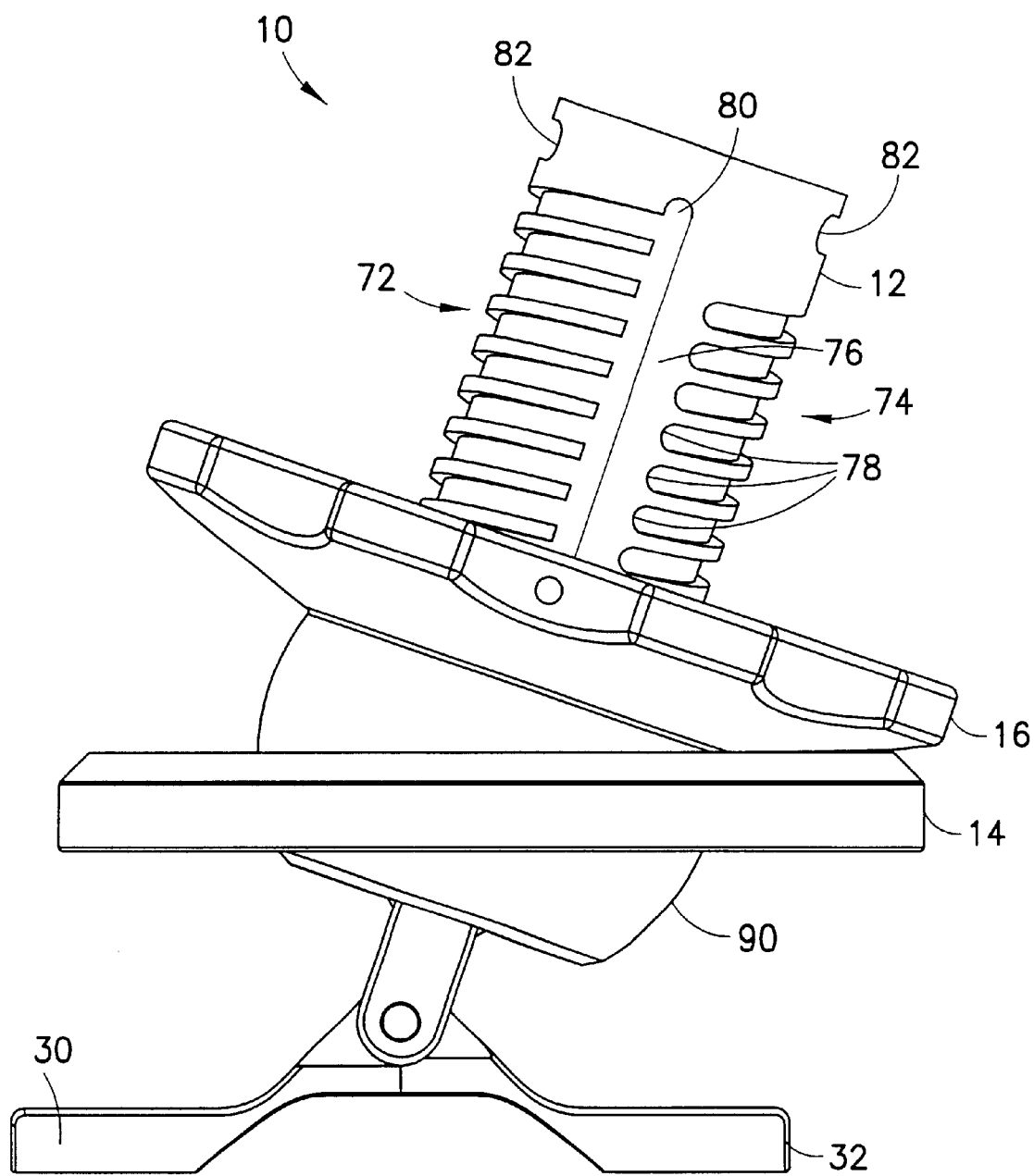
FIG. 5 is a side elevation view of the first embodiment of the port device according to the invention, shown with the swivels in an open configuration, and the port body angled relative to the washer.

Referring to FIG. 5, the proximal portion 20 of the tubular body 12 includes first and second sets of interrupted helical threads (grooves) 72, 74 extending along diametrically opposite sides of the body. The interruption 76 in the threads creates stops 78 after substantially 180° of rotation. A longitudinal groove 80 connects each set of threads 72, 74 together. The locknut 16, as described hereinafter, travels in the longitudinal grooves 80 and the threads 72, 74.

Referring now to FIGS. 1, 4 and 5, the proximal end 20 of the body 12 includes a coupling structure, e.g., the holes 82 of a ball latch, for removably coupling thereto the heart stabilizer the hereinafter described port introducer, or other device, as described in detail below.

The washer 14 is preferably disc-shaped and has a central opening 84 permitting the washer to fit about the tubular body 12 and provides an external clamping structure which operates in conjunction with the swivels 30, 32 to clamp human tissue therebetween, as described further below.

Figure 6:
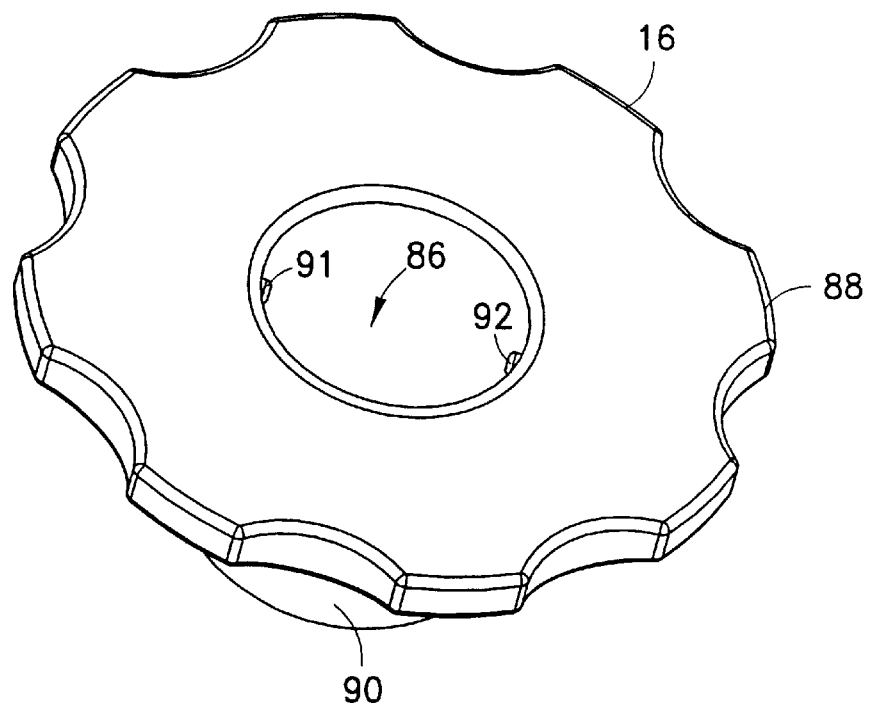
FIG. 6 is a top perspective view of a locking nut according to a first embodiment of a port device according to the invention.

Referring to FIGS. 1 and 6, the locknut 16 includes a central opening 86, a handle portion 88, and a ball portion 90. Two nubs 91, 92 radially extend into the central opening and are sized to ride within the threads 72, 72, 74 and longitudinal grooves 80 on the proximal portion of the tubular body 12 (FIG. 5). As such, when each nub 91, 92 is positioned within a respective longitudinal groove 80, the locknut 16 may be moved quickly over the port body 12 and then rotated to thread the nubs 91, 92 into the threads 72, 74 to secure the locknut 16 at a desired location over the body 12. One preferred manner of forming the nubs 91, 92 includes providing two diametrically opposite radial holes 94 in the handle portion 86 and inserting peg 98 into each radial hole such that the pegs extend into the central opening 86 to form the nubs. The ball portion 90 is a truncated sphere in shape and defines a diameter slightly larger than the diameter of the central opening 84 of the washer 14. Referring to FIGS. 1 and 5, the washer 14 is thereby adapted to articulate on the ball portion 90 of the locknut 16.

Figure 9:
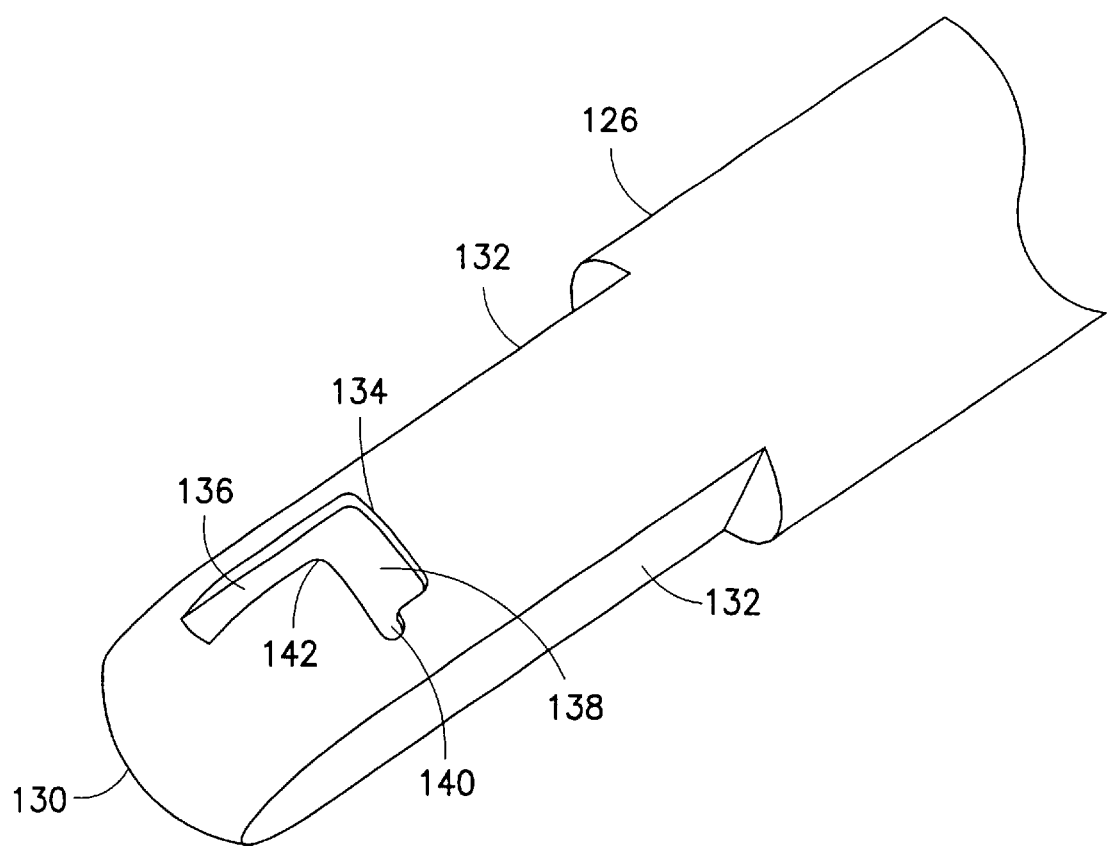
FIG. 9 is an enlarged perspective view of the distal end of the introducer of FIG. 7.

Turning to FIGS. 7 and 8, an introducer 100 adapted to introduce the port device into an incision in the chest wall and also to effect movement of the swivels between closed and open configurations is shown. The introducer 100 includes a central tubular handle 102, a proximal cap 104, and a mandrel 106 extending through the handle 102 and coupled to the cap 104. The handle 102 includes a proximal stop notch 107, and distal smaller diameter portion 108 including two diametrically-opposed hemispherical latch elements 110 for engagement within holes 82 of the port body 12, and which together form a ball latch. The latch elements 110 are provided on fingers 112 of the handle 102, which under radial force are moved radially inward. The cap 104 includes a tubular portion 114 provided with a radial hole 116, and a knob 118 which is relatively larger in diameter than the tubular portion. The tubular portion 114 of the cap 104 extends into the handle and the knob 118 seats on the proximal end 119 of the handle. The mandrel 106 includes a cylindrical shaft 120 provided with a radial bore 122 and two diametrically-opposed distal planar portions 124, and a distal actuator 126. The shaft 120 extends through the handle 102 and into the cap 104. A crosspin 128 is positioned through the radial hole 116 and into radial bore 122 securing the shaft 120 of the mandrel 106 and the cap 104 together. In addition, the crosspin 128 extends into the stop notch 107 limiting rotation of the knob (and mandrel) relative to the handle 102. The planar portions 124 provide space to permit radial movement of the latch elements 110 when the fingers 112 of the handle 102 are compressed. Referring to FIGS. 7 through 9, the actuator 126 of the mandrel 106 includes a preferably blunt end 130 and a pair of diametrically-opposed substantially planar sides 132 about the end 130. A pair of diametrically-opposed actuation grooves 134 are provided between the planar sides 132. The actuation grooves 134 are generally L-shaped and include a longitudinal portion 136 which terminates at the blunt end 130, and a transverse portion 138. The transverse portion 138 includes a notch 140.

Figure 10:
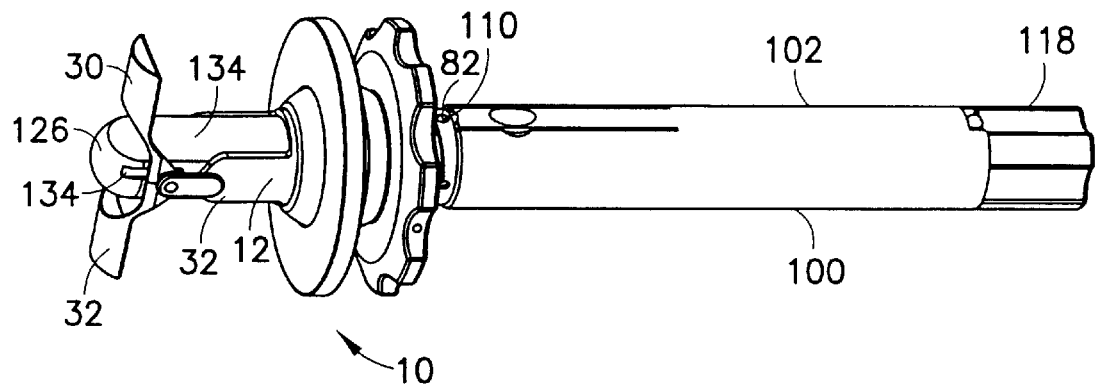
FIG. 10 is a side perspective view of introducer coupled to the port device according to the invention, with the swivels shown in an open configuration.
Figure 11:
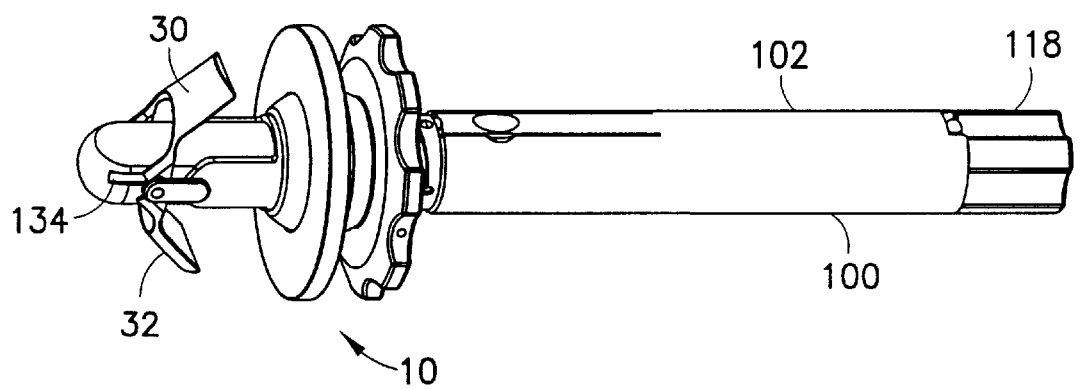
FIG. 11 is a view similar to FIG. 10 with the swivels shown in a partly closed configuration.
Figure 12:
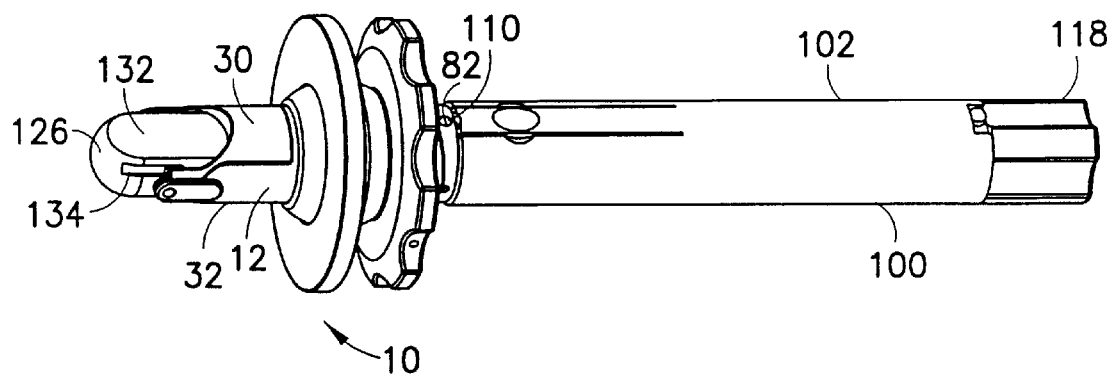
FIG. 12 is a view similar to FIG. 10 with the swivels shown in a closed configuration.

Referring now to FIG. 10, the introducer 100 is coupled to the port device 10 by opening the swivels 30, 32 of the port device and inserting the actuator 126 of the introducer until the ball latch engages; i.e., the proximal end of the port device rides over the latch elements 110 until the latch elements catch in the holes 82 in the port body 12. With the swivels 30, 32 in the open configuration, the levers 62 (FIG. 2) are also aligned within respective longitudinal portions 136 of the actuation grooves 134 and reside therein. More particularly, the pivot axis $A_p$ of the levers 62 are located just proximal of the inner corners 142 of the grooves (FIGS. 2 and 9). Referring to FIGS. 2, 9, 11 and 12, while keeping the handle 102 fixed, the knob 118 is rotated in a clockwise direction (causing movement of the grooves 134 relative to the levers 62. The corners 142 contact the levers 62 and rotate the levers into the transverse portions of each of the grooves, thereby effecting closing of the swivels about the port body 12. One end of each lever engages a notch 140 in its respective groove 134 to "lock" the levers (and swivels) in the closed position until the knob is rotated in an opposite direction. The amount of the rotation of the knob 118 relative to the handle 102 required to effectuate the closing is relatively limited, e.g., approximately twenty-four degrees with groove 134, and contact of the crosspin 128 against the top notch 107 limits the movement.

Figure 31:
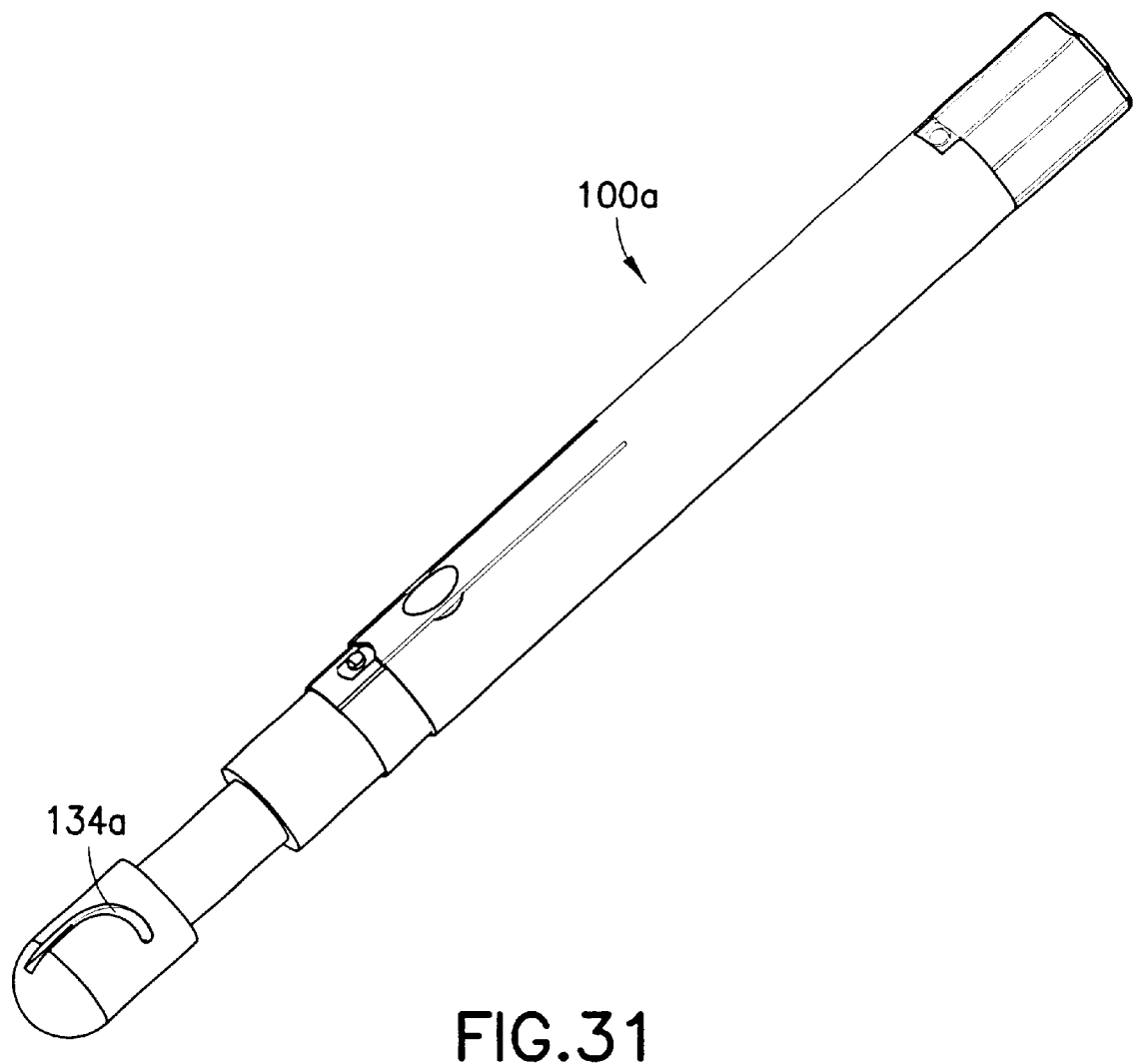
FIG. 31 is a perspective view of a second embodiment of a port introducer according to the invention.

The introducer may be provided with other shaped grooves, the rotation of which effects movement of the levers and swivels. For example, referring to FIG. 31, the J-groove 134a on the introducer 100a operates to close (or open) the swivels by clockwise rotation of approximately 45°.

The planar sides 132 of the actuator 126 are so shaped such that the swivels 30, 32 may rest there against when the swivels are in the closed configuration (FIG. 12) and thereby permit the outer surface of the swivels to effectively complete the circumference of the tubular body of the port device.

Once the swivels are locked in a closed configuration about the introducer 100, the introducer may be manipulated to introduce the port device 10 into an incision in a chest wall, preferably between two ribs, or an incision in another area of human tissue. To secure the port within the incision, the knob 118 is rotated in a counter-clockwise direction, releasing the ends of the levers from the notch 140 and causing the levers to ride against their respective walls of longitudinal portions 136 and rotate about their pivot axis $A_p$. This results in aligning the levers 62 within the longitudinal portions 136 of the grooves 134 and moving the swivels into the open configuration (FIG. 10). In the open configuration, it is preferable that the swivels each be located under a respective rib. The port body 12 is pulled back to contact the ribs and then the washer 14 is moved against the outer surface of the tissue surrounding the incision. The nut 16 is advanced through the longitudinal grooves 80 to contact and press against the washer and then threadably rotated within the threads 72, 74 to lock against the washer. The swivels and washer thereby provide a clamping action about the ribs and tissue and stably secure the tubular body 12 of the port device within the chest wall.

The introducer 100 is then released from the port body 12 by depressing the fingers 112 of the handle 102. Finally, the introducer is withdrawn leaving an open port through which a surgical instrument other device may be introduced, and to which a device may be securely coupled. It will be appreciated that due to the articulating relationship of the ball portion 90 of the lock nut 16 and the washer 14, the tubular port 12 may be articulated relative to the washer, and the chest wall.

The port device may be removed from the body by reinserting the introducer in the port device such that the levers align with and enter the longitudinal grooves. The introducer is preferably coupled to the tubular-body. The locknut is released, and the port device is moved slightly into the chest cavity to provide space for the swivels to fold. Then the knob of the introducer is rotated relative to the handle to cause the actuator to rotate relative to the swivels, and cause the swivels to fold against the tubular body into the closed configuration. The introducer and port device are then together withdrawn from the chest wall of the patient.

Figure 13:
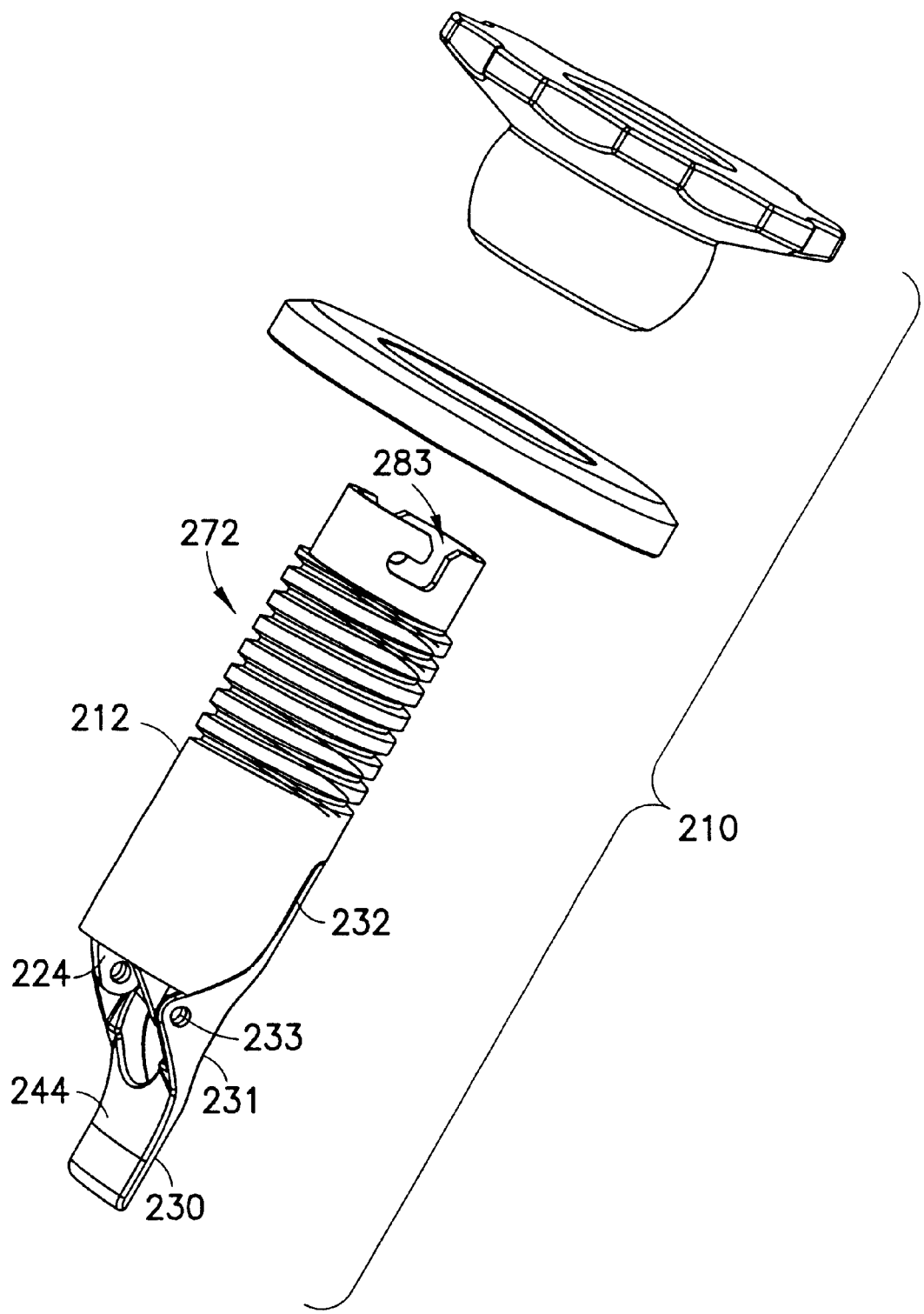
FIG. 13 is an exploded side perspective view of a second embodiment of a port device according to the invention, with the swivel shown in a closed configuration.
Figure 14:
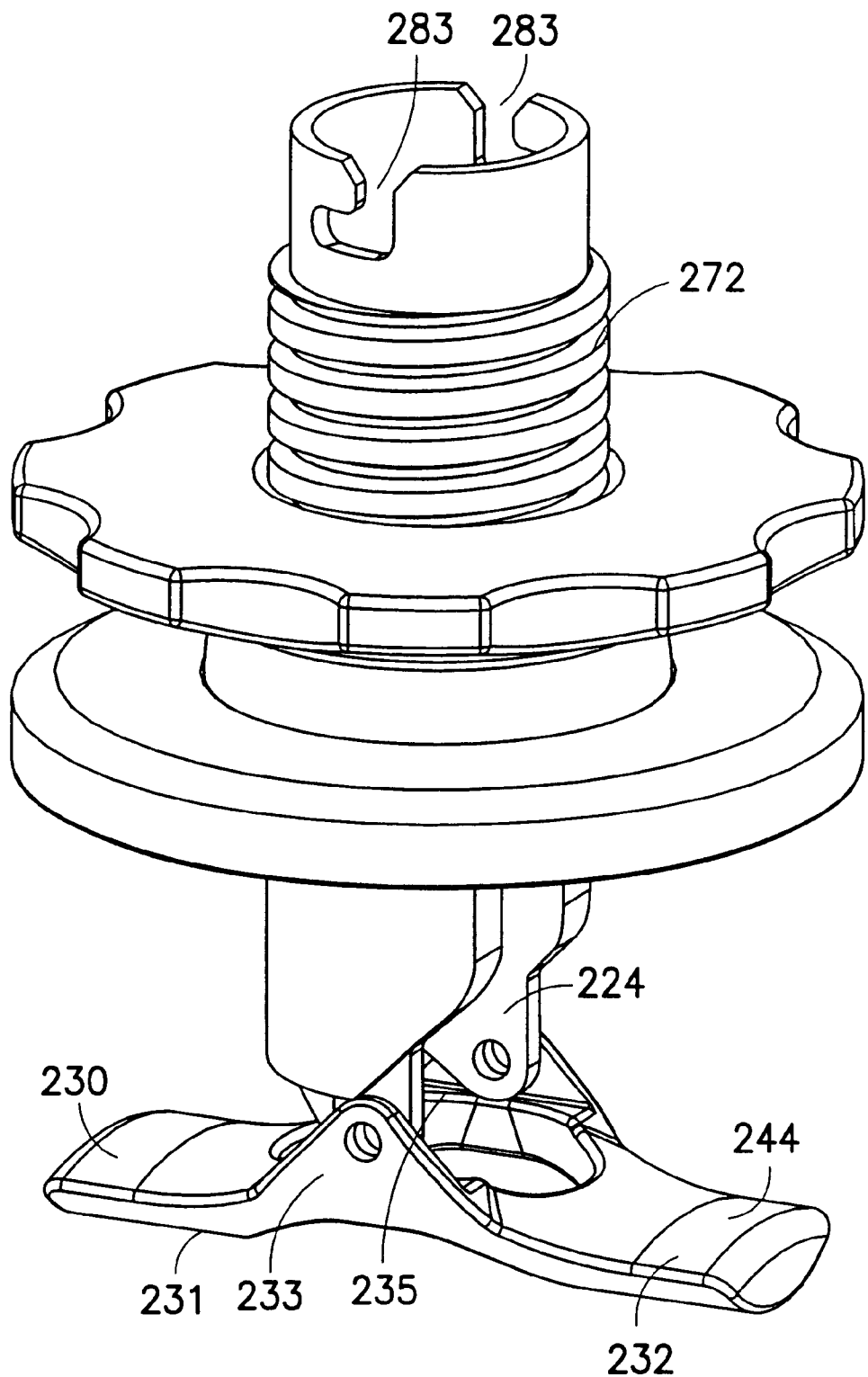
FIG. 14 is a top perspective view of the second embodiment of the port device, with the swivel shown in an open configuration.
Figure 15:
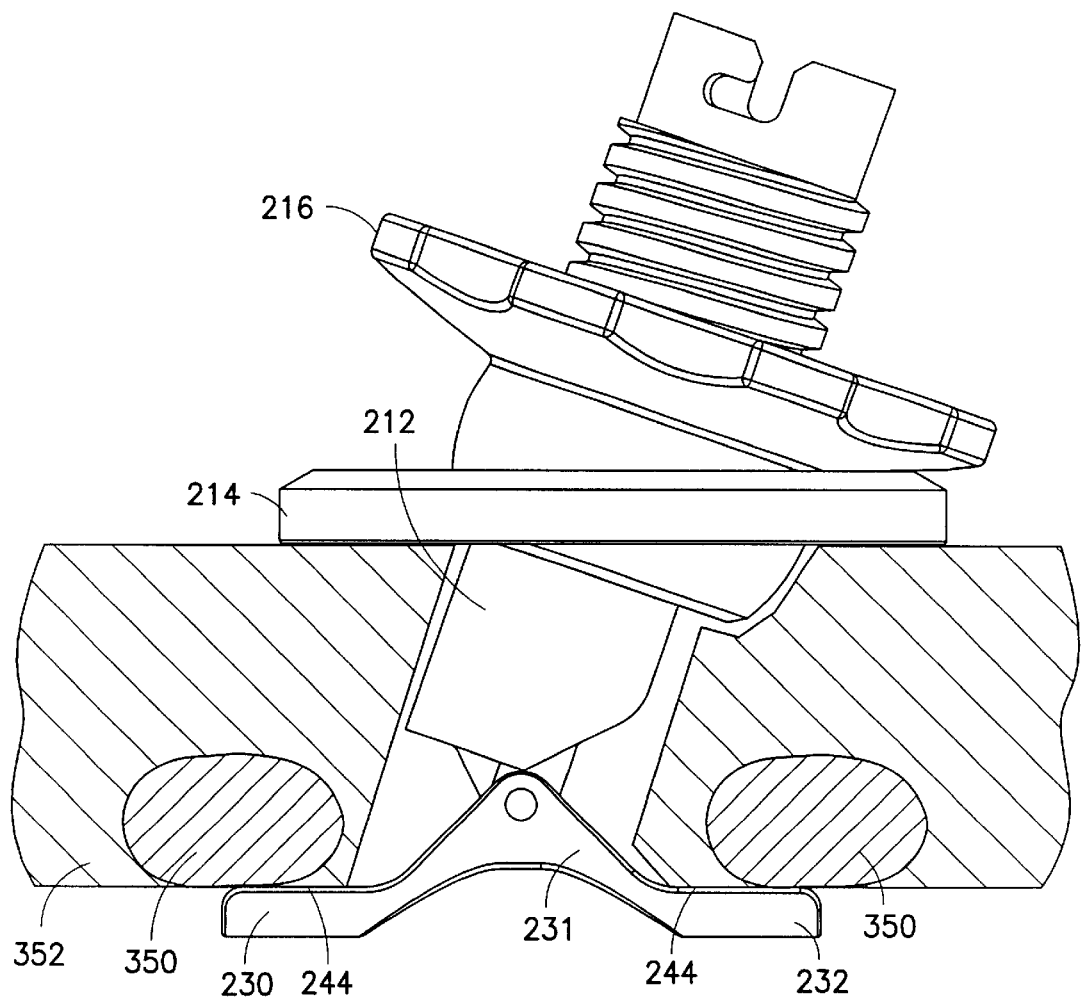
FIG. 15 is a side perspective of a second embodiment of the port device shown inserted in body tissue and between ribs of a patient.

Turning now to FIGS. 13 and 14, a second embodiment of a port device 210 according to the invention substantially similar to the first embodiment (with like parts having reference numerals incremented by 200) is shown. The tubular body 212 of the port device 210 includes a double helix thread 273 without interruptions. The proximal end of the port device includes a female bayonet coupling 283. The distal end of the tubular body includes a single swivel 231 including two arms 230, 232 and rotatably coupled at a central portion 233 to a clevis 224 formed at the distal end of the body. The inner contact surfaces 244 of the swivel are preferably provided with a contour to facilitate placement of the swivels against the ribs even when the tubular body is articulated through various angles relative to the washer. The swivel 231 is preferably biased with a spring 235 to move into an open configuration substantially perpendicular to the tubular body. As such, during insertion, a mandrel (not shown) is preferably positioned within the tubular body, and may be coupled to the female bayonet coupling, to maintain the swivel in a closed configuration substantially parallel to the tubular body. Then, when the proximal end of the swivel 231 is past the ribs (see FIG. 15), the mandrel is removed from the tubular body, and the spring 235 automatically rotates the swivel 231 into the open configuration with the swivel being captured by the ribs 350. The washer 214 and locknut 216, which are preferably the same as described in the first embodiment, are then tightened against the tissue 352 (as shown in FIG. 15), clamping the ribs 350 and tissue 352 between the washer and swivel.

The swivel 231 may be returned to the closed configuration for removal from the patient body by loosening the locknut and washer, pushing the swivel distally into the chest cavity, and inserting the mandrel back through the tubular body and causing contact against an arm of the swivel to force the swivel to rotate back into the closed configuration.

Figure 32:
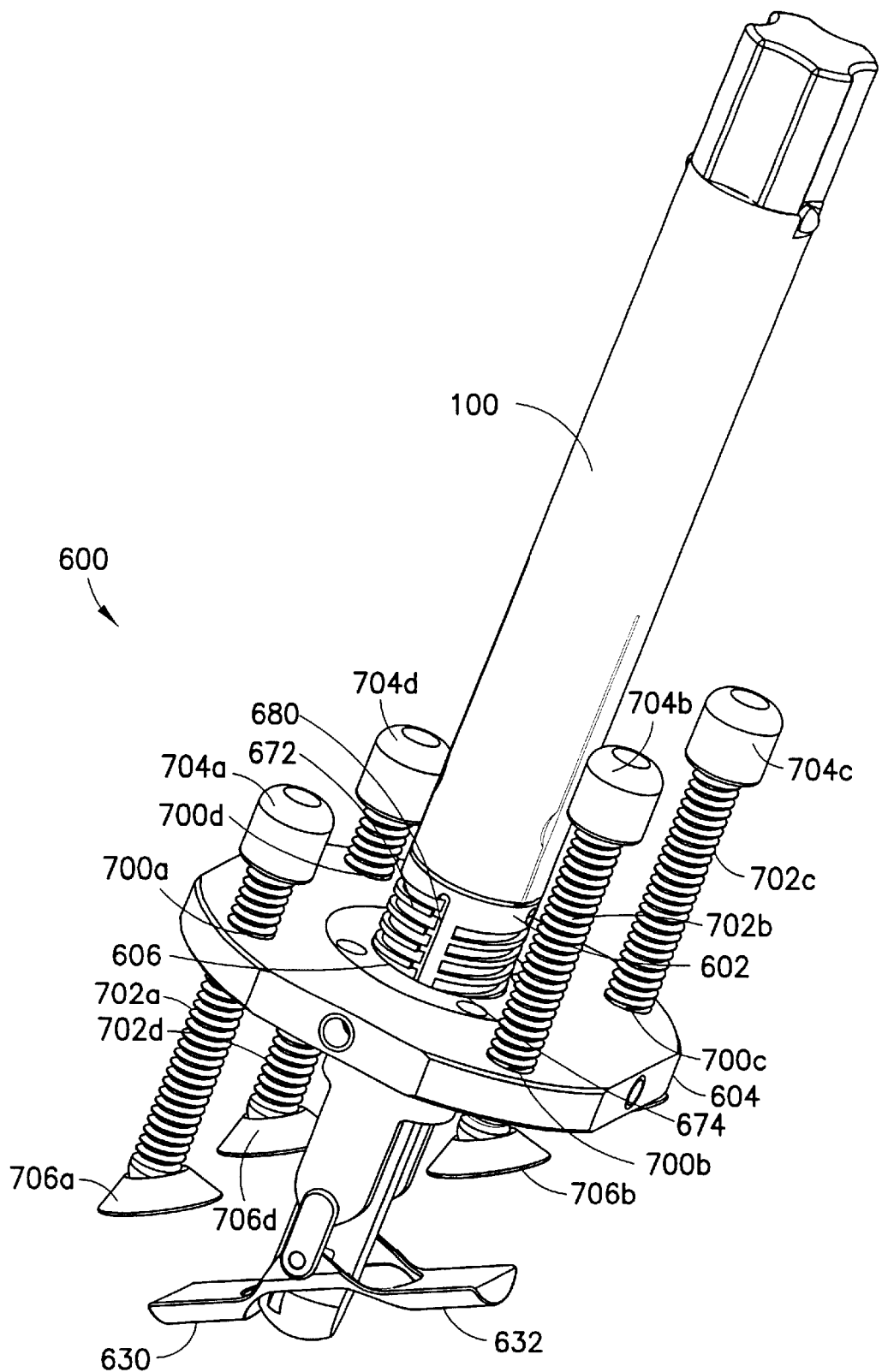
FIG. 32 is a perspective view of a third embodiment of a port device according to the invention.

Turning now to FIG. 32, a third embodiment of a port device 600 according to the invention is shown. The port device includes a tubular body 602 and an adjustable platform 604. The tubular body 602 includes swivels 630, 632 at a distal end thereof, and threads 672, 674 and longitudinal grooves 680 along the body, preferably the same as those described with respect the first embodiment. The platform 604 includes a central opening 606 and nubs which extend into the opening (the nubs are not shown, but are substantially similar to nubs 91, 92 in the first embodiment). The nubs permit the platform to travel in the longitudinal grooves 680 and threads 672, 674 to move and threadably lock the platform relative to the body 602. The platform 604 also includes a plurality of, e.g., four, threaded bores 700*a–d* preferably equally spaced about the central opening 606. Bolts 702*a–d* are thread partially through the bores 700*a–d*, and each is provided with a proximal handle 704*a–d* by which the bolt may be manually rotated, and a distal foot 706*a–d* pivotable about the end distal end of the bolt.

An introducer 100, shown coupled to the port device 600, is preferably utilized to insert and deploy the swivels 630, 632 of the port device 600 into the chest wall, and is then disengaged and removed from the port. The platform 604 is then angularly adjusted relative to the chest wall by rotating the bolts. That is, if it is desired to have the platform 604 be oriented substantially planar with the chest wall, each bolt 702*a–d*, by rotation of its respective handle 704*a–d*, is tightened by substantially the same amount to cause the chest wall to be evenly clamped between the swivels 630, 632 and the feet 706*a–d*. However, if it is desired to cause the platform, and port body 602 therein, be at an angle relative to the chest wall (to provide better access to the surgical site), the bolts 706*a–d* may be thread into the bores 700*a–d* by different amounts to cause the platform 604 to assume a desired angle relative to the chest wall.

Figure 33:
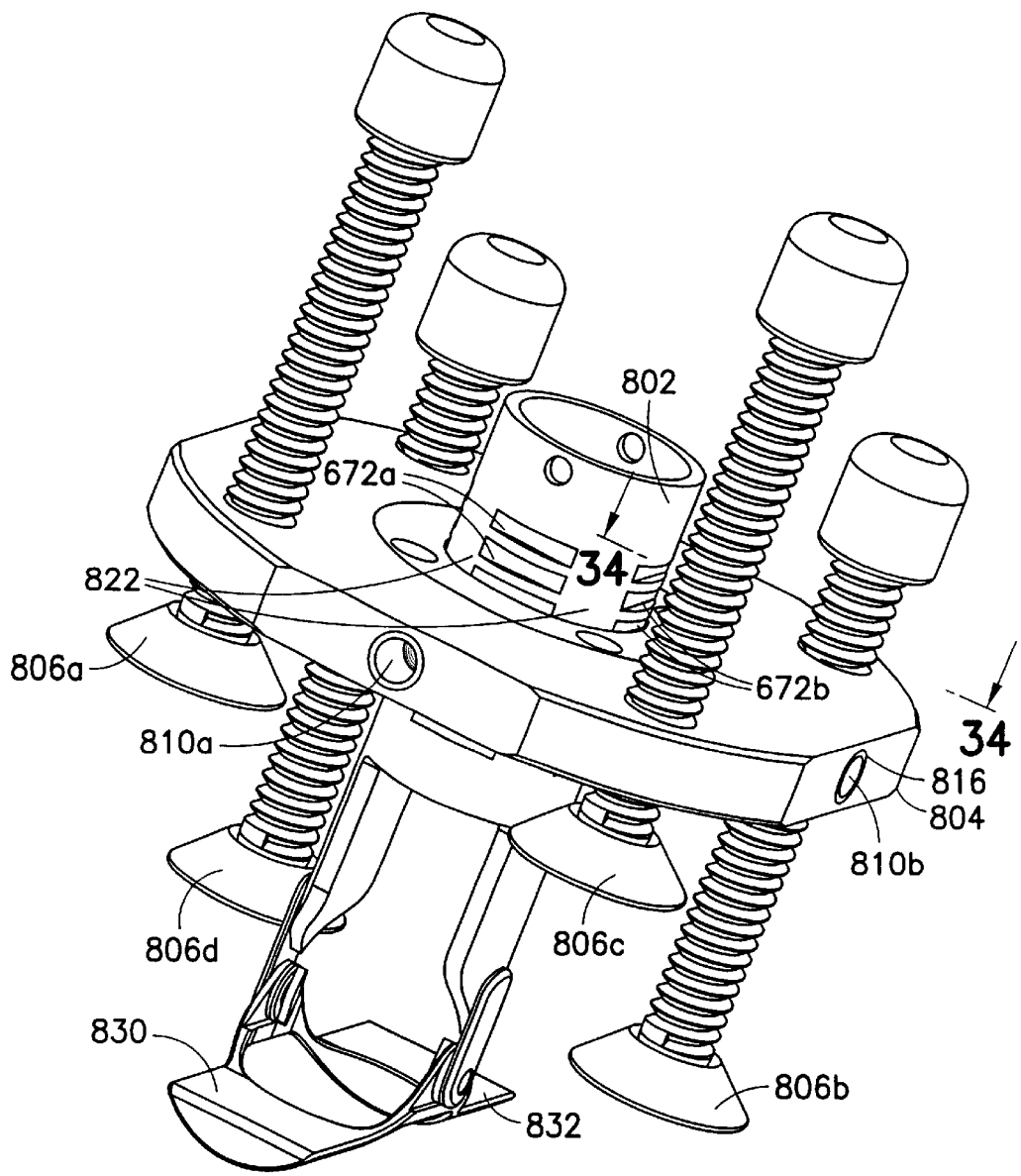
FIG. 33 is a perspective view of a fourth embodiment of a port device according to the invention.
Figure 34:
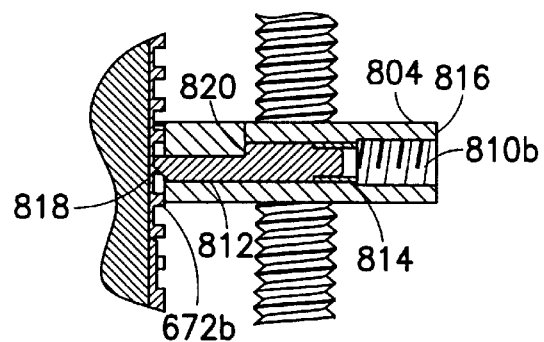
FIG. 34 is a partial section view across line 34—34 in FIG. 33 of the tubular body of the fourth embodiment of the port device of the invention.

Referring now to FIGS. 33 and 34, a fourth embodiment of a port device 800 according to the invention, substantially similar to the third embodiment 600, is shown. The tubular body 802 of the port device is provided with four sets of grooves 672*a*, 672*b* (672*c* and 672*d* not shown but located diametrically opposite 672*a* and 672*b*, respectively), rather than the threads 672, 674 of body 602 (FIG. 32). Each set of grooves 672*a–d* extends parallel to a respective tangent on the surface of the body and offset by ninety degrees about the body. The platform 804 includes four radial channels 810*a*, 810*b* (810*c* and 810*d* not shown) located ninety degrees apart. A ratchet pin 812 is provided in each of the channels 810*a–d*. A spring 814 is positioned within each channel 810*a–d* to bias each ratchet pin 812 toward a respective set of grooves 672*a–d*, and a locking collar 816 maintains the spring within the channel. The ratchet pin 812 is shaped to include a beveled edge 818 facilitating radial outward movement of the ratchet pin against the bias of the spring when the platform is moved distally over the grooves of the tubular body. In addition, the ratchet pin includes a stop 820 to limit inward radial movement. This configuration permits the platform to be readily and rapidly moved distally along the tubular body to a desired location with the ratchet pins locking within the grooves to prevent proximal movement of the platform, and thereby clamping the chest wall between the swivels 830, 832 and the feet 806*a–d* coupled to the platform. The feet may then be adjusted to orient the platform at an angle relative to the chest wall.

When it is desired to release the platform from about the tubular body, the feet are loosened from against the chest, and the platform is rotated approximately forty-five degrees such that the ratchet pins lie along smooth portions 822 of the tubular body. The platform may then be moved proximally relative to the tubular body without substantial resistance.

Figure 16:
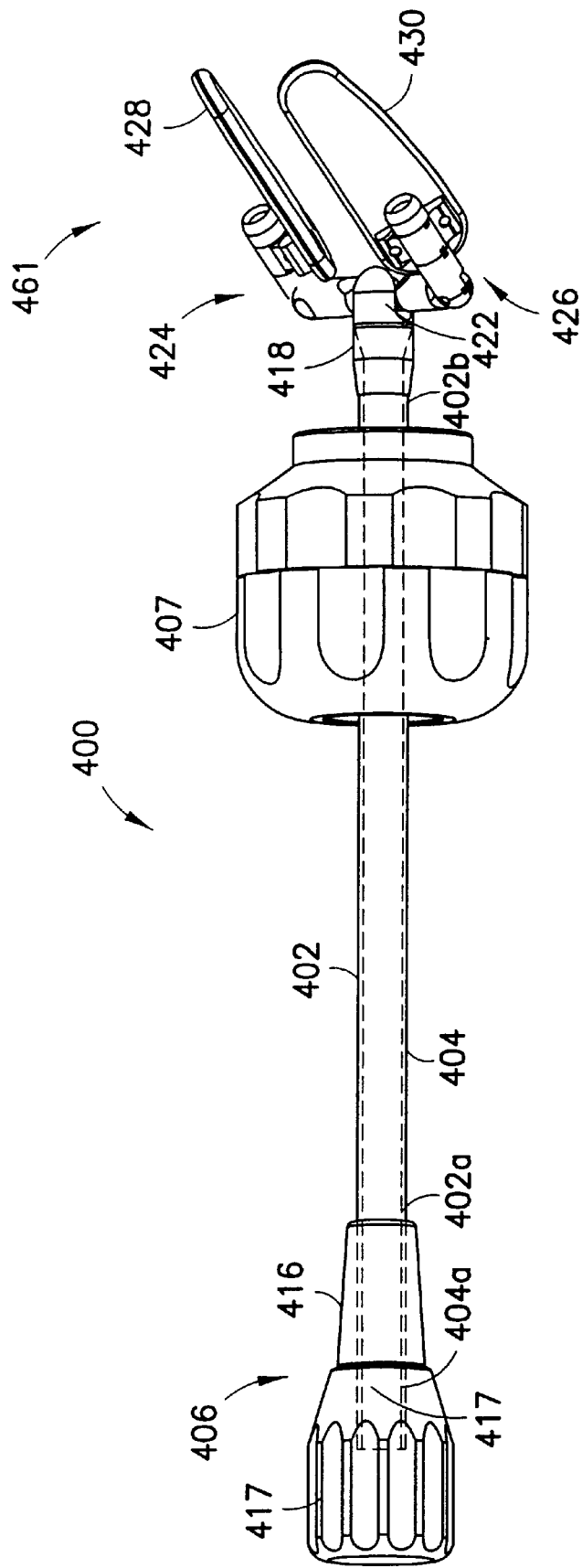
FIG. 16 is a side perspective view of a first embodiment of a heart stabilizer device according to the invention.

Turning now to FIG. 16, a first embodiment of the heart stabilizer 400 preferably includes a hollow shaft 402, a rod 404 extending through the shaft, and a proximal control handle 406 coupled to the proximal ends of the shaft 402, and rod 404 to move the rod longitudinally within the shaft, as described in more detail below. The shaft 402 and rod 404 are keyed (not shown) such that the rod cannot rotate relative to the shaft. A shaft lock 407 is provided about the shaft 402 and operates to lock the heart stabilizer 400 to a port device, such as port devices 10 (FIG. 1) and 210 (FIG. 13), and also permits locking the shaft 402 in numerous longitudinal and angular positions relative to the port device.

Figure 17:
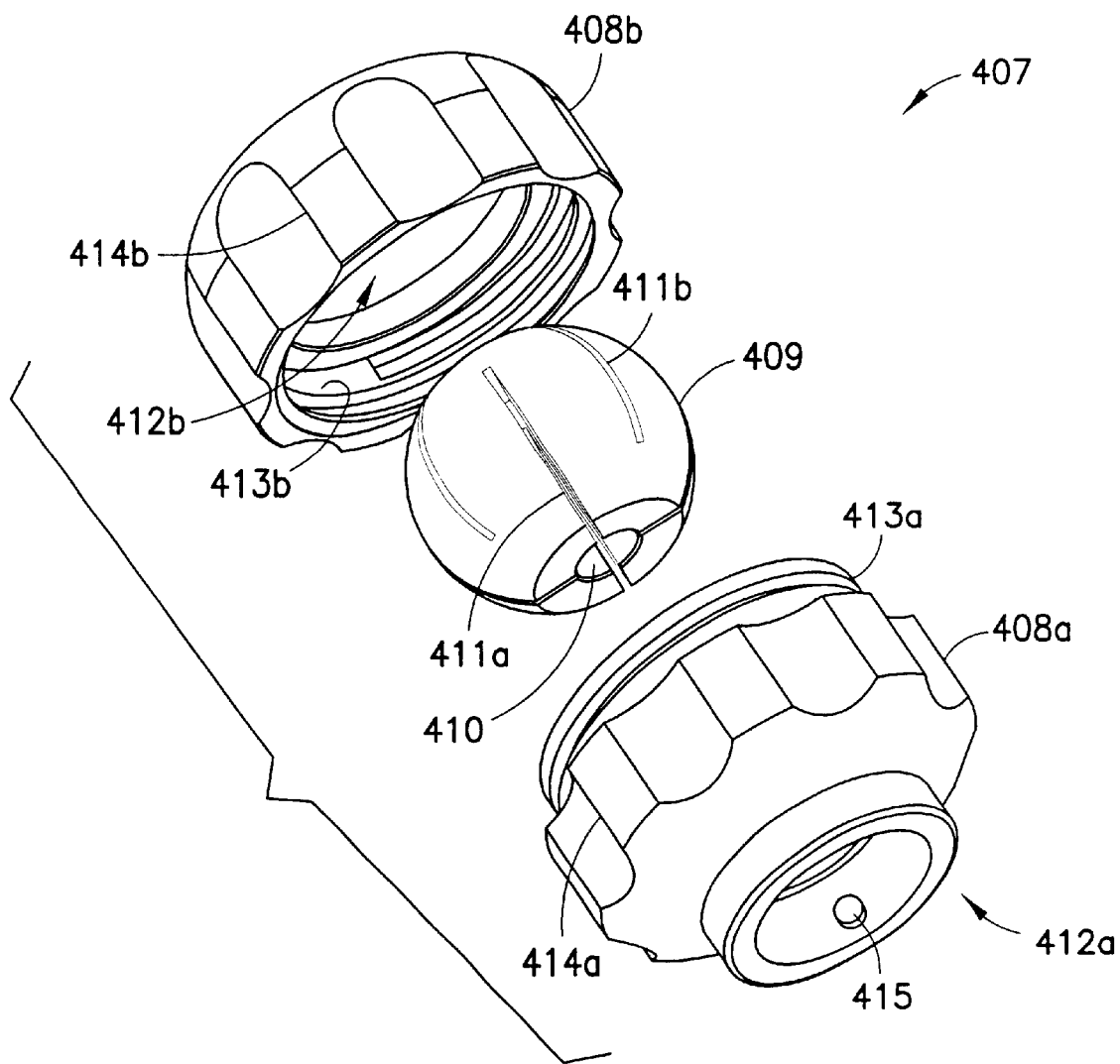
FIG. 17 is an exploded perspective view of the shaft lock of the heart stabilizer device of FIG. 16.

More particularly, referring to FIGS. 16 and 17, the shaft lock 407 includes a port connector 408*a*, a cap 408*b*, and a ball element 409 between the port connector and cap. The ball element 409 includes a shaft bore 410, a first set of diametric slots 411*a* in one end of the ball element, and a second set of diametric slots 411*b* in the other end of the ball element. The two sets of slots 411*a* and 411*b* permit radial compression of the ball element 409 to cause the diameter of the shaft bore 410 to decrease. The port connector 408*a* and cap 408*b* each include an opening 412*a*, 412*b*, a mating means 413*a*, 413*b*, e.g., threads, for mating with each other, and a finger gripping structure 414*a*, 414*b* to facilitate relative rotation of the port connector and cap about the mating means. The port connector 408*a* also includes a port mating structure 415, e.g., a bayonet, for mating with the female bayonet coupling 283 of a port 210 (FIG. 14). The shaft 402 extends through the shaft bore 410 and, when the port connector 408*a*, 408*b* are loosely mated with each other, the shaft and ball element 409 may be pivoted relative to the port connector and cap, and the shaft may be moved longitudinally within the bore 410 relative to the shaft lock. When the cap 408*b* is tightened on the port connector 408*a*, the ball element 409 and shaft 402 are locked in their respective positions.

Referring to back to FIG. 16, the control handle 406 includes a knob mount 416 fixedly coupled to the proximal end 402*a* of the shaft 402, and a knob 417 rotatably coupled to the mount 416. The knob 416 includes a threaded bore 417, and the proximal end 404*a* of the rod 404 is threaded, and threadably engaged within the bore of the knob 417. The rotation of the knob 417 relative to the mount 416 causes the rod 404 to move longitudinally relative to the shaft 402, as the keyed rod cannot rotate relative to the shaft.

Figure 18:
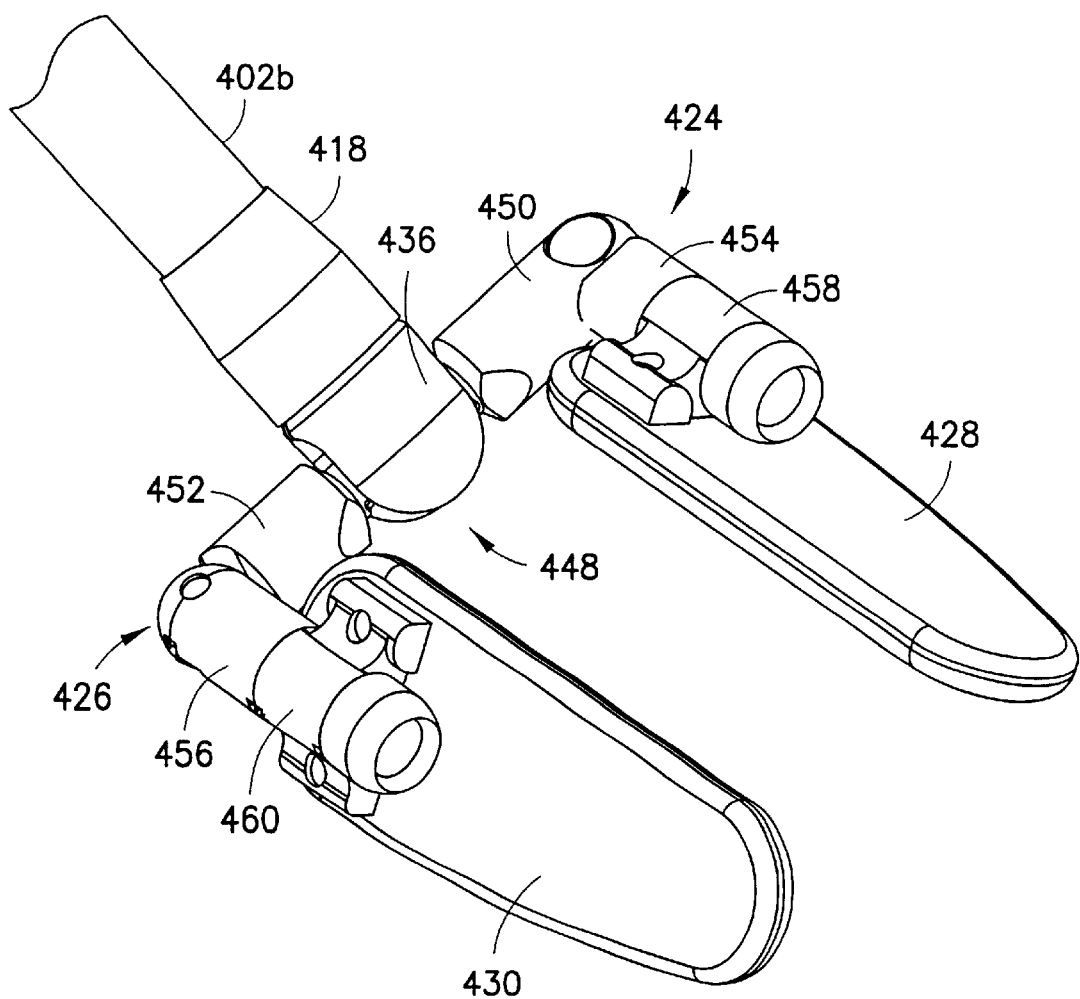
FIG. 18 is a perspective view of the stabilizing mechanism at the distal end of the heart stabilizer device of FIG. 16.
Figure 19:
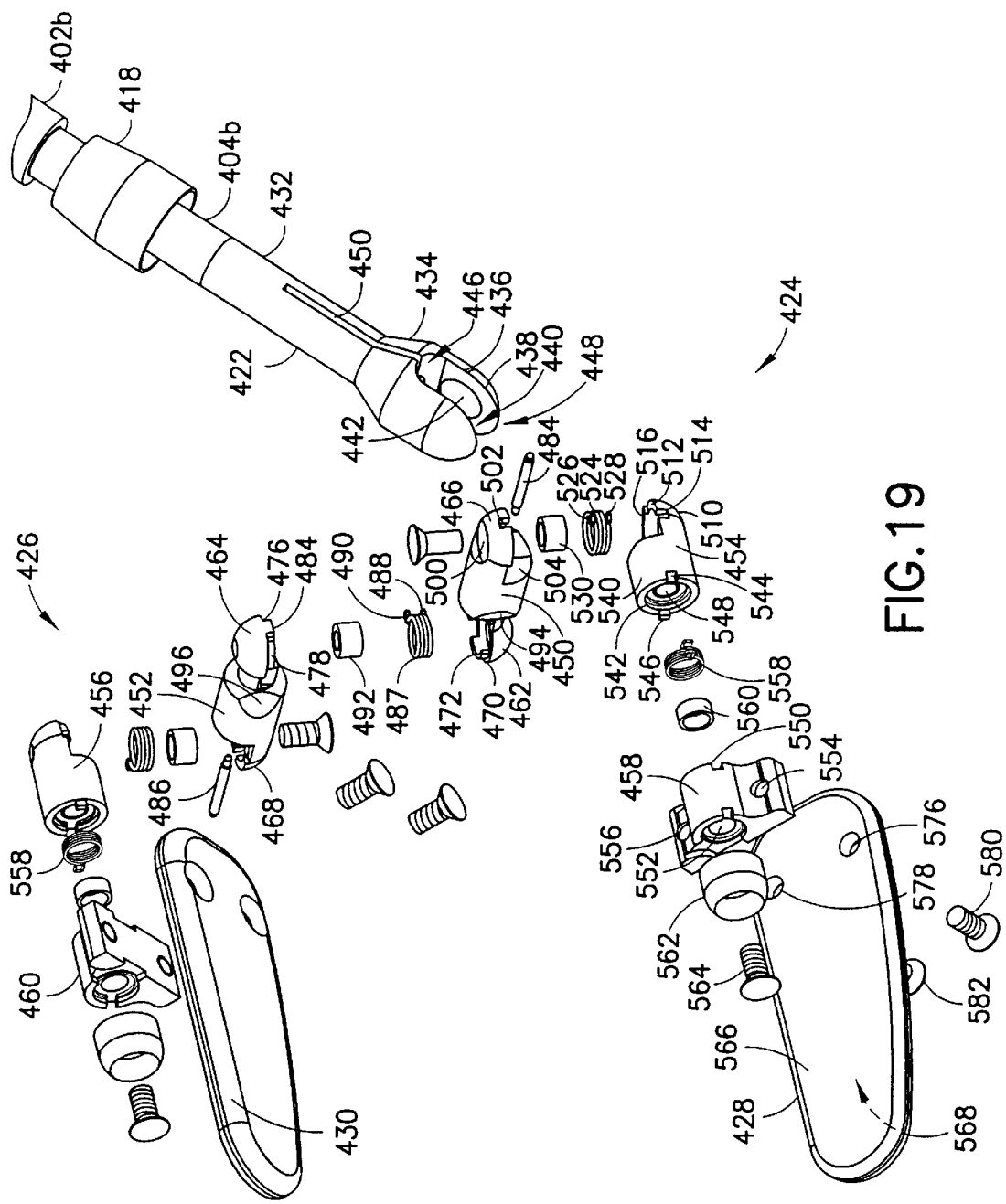
FIG. 19 is an exploded perspective view of the stabilizing assembly of the heart stabilizer device of FIG. 16.

Referring now to FIGS. 16, 18 and 19, the distal end 402*b* of the shaft 402 is provided with a collar 418. The distal end 404*b* of the rod 404 is coupled to a clevis 422. The clevis 422 includes a post portion 432 coupled to the rod 404, a frustoconical portion 434, and a U-shaped socket 436 including side walls 438, 440 with spherical concavities 442, a back wall 446, and a front opening 448 extending through an approximately 180° arc. A slot 450 extends from the back wall 446, through the frustoconical portion 434, and into the post portion 432. When the rod 404 is moved proximally relative to the shaft 402, by operation of the handle 406, the collar 418 rides against the frustoconical portion 434 of the clevis 422, causing compression of the socket 436. Conversely, when the rod 404 is moved distally relative to the shaft 402, the frustoconical portion 434 of the clevis 422 is released from the collar, permitting the socket 436 to slightly expand.

Referring to FIGS. 18 through 21, two articulating arms 424, 426 are coupled in the socket 436 of the clevis, and a rotatable stabilizing foot 428, 430 is coupled to the end of each arm. The first and second articulating arms 424, 426 each include an upper arm 450, 452, a lower arm 454, 456, and a wrist mount 458, 460. Stabilizing feet 428, 430 are coupled to the wrist mounts, 458, 460, respectively. The articulating arms 424, 426 and the feet together define a stabilizing assembly 461.

More particularly, each of the first and second upper arms 450, 452 includes a partly hollow, generally hemispherical shoulder 462, 464 at one end and an upper elbow portion 466, 468 at the other end. The first shoulder 462 (of the first upper arm) includes rim 470 defining a first upper cam 472, and the second shoulder 464 (of the second upper arm) includes a rim 476 defining a second upper cam 478. In addition, each of the first and second upper arms includes a pin bore 480, 482 extending longitudinally through the arms. Lock pins 484, 486, which function to limit the movement of the first and second upper arms 450, 452 relative to each other as described in more detail below, are provided within the pin bores 480, 482.

The first and second shoulders 462, 464 are oriented and configured such that they together substantially define a sphere. A shoulder spring 487 is positioned within the sphere defined by the shoulders, and the ends 488, 490 of the spring 487 are coupled to and about the rims 470, 476, respectively, with the spring 487 under helical compression to urge the upper arms 450, 452 away from each another. A spacer 492 is provided within the spring 487 to stabilize the spring within the shoulders. The shoulders together are provided in the socket 436, with each hemispherical shoulder residing partially within a respective one of the concavities 442. While the shoulders 462, 464 appear to form a ball within the socket 436, it will be appreciated that the shoulders provide additional function over a ball in that the two upper arms 450, 452 are permitted to independently rotate relative to each other at the shoulders. The spring 487 is adapted to bias the upper arms 450, 452 into an open position in which the two are in alignment; i.e., at substantially 180° relative to each other. Each upper arm 450, 452 also includes a front bevel 494, 496. As such, when the upper arms are moved against the bias of the spring 487 toward each other, an angle α as small as approximately 45°, and preferably 47°, may be defined therebetween (FIG. 20), with the bevels 494, 496 minimizing interference between the two upper arms which would otherwise limit the ability to define such a small angle α therebetween.

The description of the lower arms 454, 456 and the coupling of the lower arms to the upper arms will now be described with respect to upper arm 450 and lower arm 454 of the first articulating arm 424, with it being understood that the lower arms and their couplings of the second articulating arm 426 are each substantially the same as in the first articulating arm, but installed upside down relative to the first articulating arm.

The upper elbow portion 466 of upper arm 450 is rotatably coupled to a lower elbow portion of lower arm 454. The upper elbow portion 466 is generally hemispherical in shape and includes a countersunk screw hole 500 and a first elbow spring catch 502. The upper arm 454 is provided with a bevel 504 adjacent the upper elbow portion 466. The lower arm 454 includes a generally hollow, substantially hemispherical lower elbow portion 510 which mates with the upper elbow portion 466 of the upper arm 450. The lower elbow portion 510 includes a rim 512 defining a second elbow spring catch 514, and a lower arm cam 516 including a cam lock 518 and a cam stop 520. The elbow portion 510 also includes a threaded screw hole 522.

An elbow spring 524, under helical tension, is provided within the upper and lower elbow portions 466, 510. The elbow spring 524 includes ends 526, 528 which are coupled in the first and second elbow spring catches 502, 512, respectively, biasing the upper and lower arms toward a configuration having a relatively smaller angle therebetween. A tubular spacer 530 is provided within the elbow spring 524 to stabilize the spring within the shoulders and provide a pathway for a screw 532 which extends into the screw hole 500 and is threadably engaged in screw hole 522 to secure the upper and lower arms together in a manner which permits the lower arm to pivot relative to the upper arm.

The lower end of the lower arm includes an upper wrist portion 540 provided with a rim 542 oriented orthogonally to the rim 512, and a threaded bore 548. The rim 542 defines a first wrist spring catch 544 and a stop 546.

The wrist mount 458 includes a second wrist spring catch 550, a throughbore 552, and two threaded mounting holes 554, 556; one provided on either side of the throughbore 552. A wrist spring 558 is provided about a spacer 560 between the upper wrist portion and the wrist mount and engages the first and second wrist spring catches. The wrist spring 558 is biased to rotate the wrist mount 458 clockwise relative to the upper wrist portion 540 when viewed in the direction of the lower arm 454 toward the wrist mount 458. A wrist spring 558' in the second arm 426 rotates a respective wrist mount in an opposite direction such that the wrist mounts are urged to rotate away from each other.

A collar 562 is provided in alignment with the throughbore 552, and a screw 564 extends through the collar 562 and throughbore 552 and is secured in the threaded bore 548 of the upper wrist portion 540.

The foot 428 includes an outer surface 566, a contact surface 568, and two spaced apart bores 576, 578 which align with the threaded bores 554, 556 of the wrist mount 458. The foot 428 is coupled at its outer surface 566 to the wrist mount 458 with screws 580, 582 extending into the bores 576, 578 and threadably engaged within bores 554, 556 of the wrist mount 458.

Figure 20:
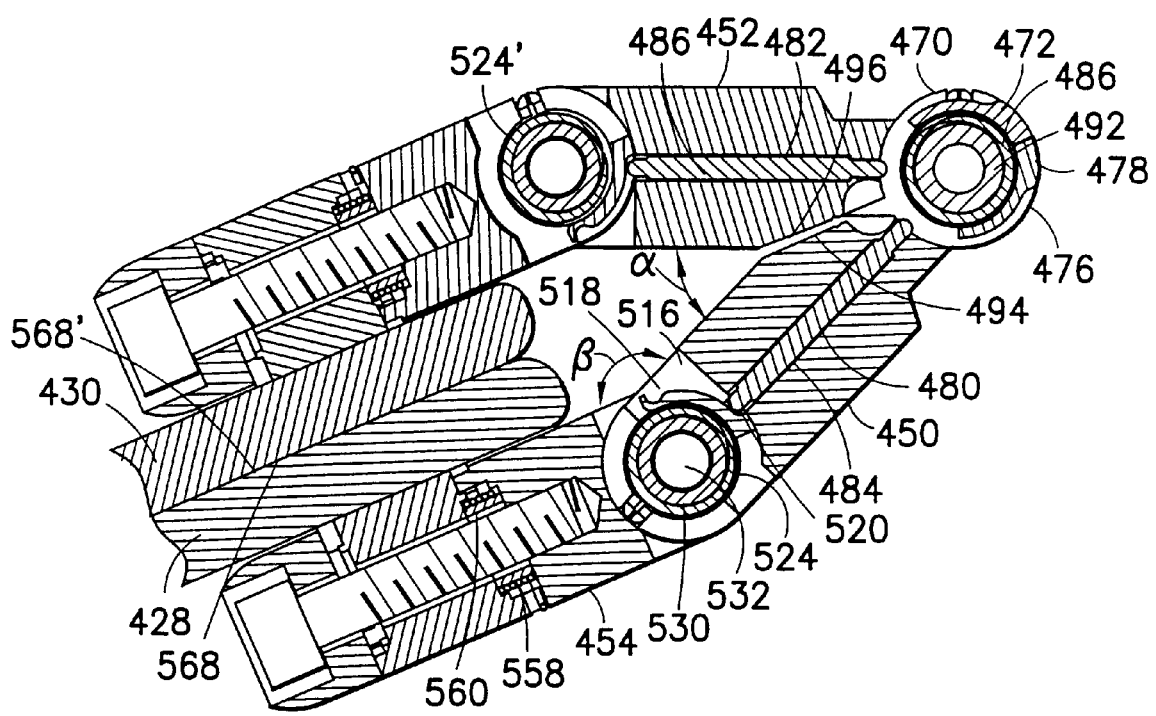
FIG. 20 is a broken longitudinal section view of the shoulders and upper arms of the stabilizing assembly of the heart stabilizer device of FIG. 16 shown in a closed position.
Figure 21:
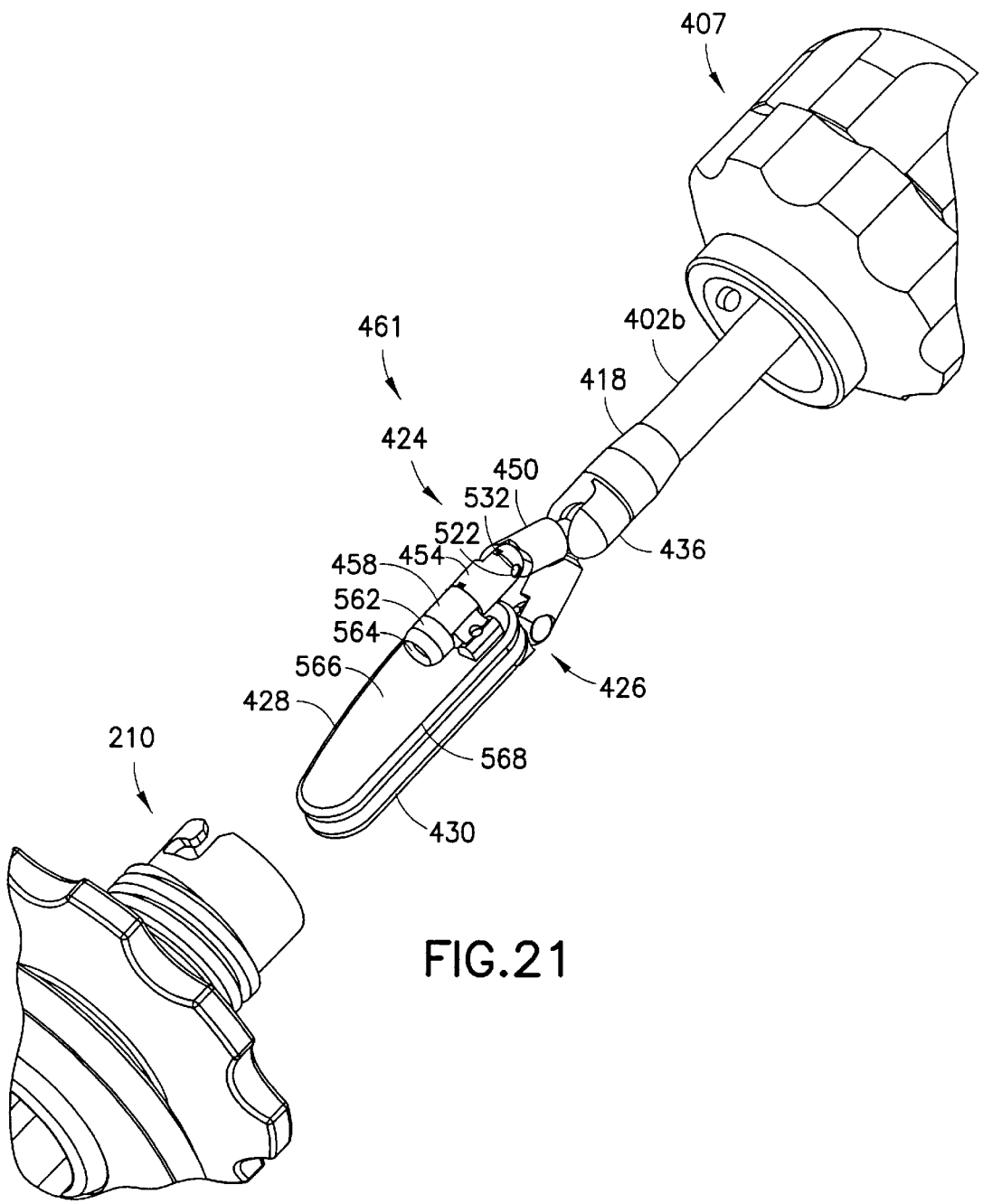
FIG. 21 is a broken bottom perspective view of the stabilizing assembly of the heart stabilizer device of FIG. 16 shown in a closed position and a port device according to the invention.

The operation of the heart stabilizer 410 and particularly the stabilizing assembly 461 will now be described, with reference numerals terminating in a prime referring to elements of the second articulating arm. Referring to FIGS. 20 and 21, the articulating arms 424, 426 and feet 428, 430 are manually folded into the illustrated configuration. That is, the upper arms 450, 452 are folded about the shoulders, and the feet 428, 430 are rotated inward toward each other such that the respective contact surfaces 568, 568' and in contact or substantially adjacent each other. In this configuration the upper arms 450, 452 have an angle α of approximately 47°, and the feet 428, 430 are oriented substantially parallel to the shaft 402 of the heart stabilization device 410. The handle 406 is then operated to cause the collar 418 to compress the socket 436 about the shoulders 462, 464 of the upper arms and thereby lock the upper arms 450, 452, lower arms 454, 456, and feet 428, 430 in their relative positions and present a relatively small cross-sectional area for insertion through a port 210.

Figure 22:
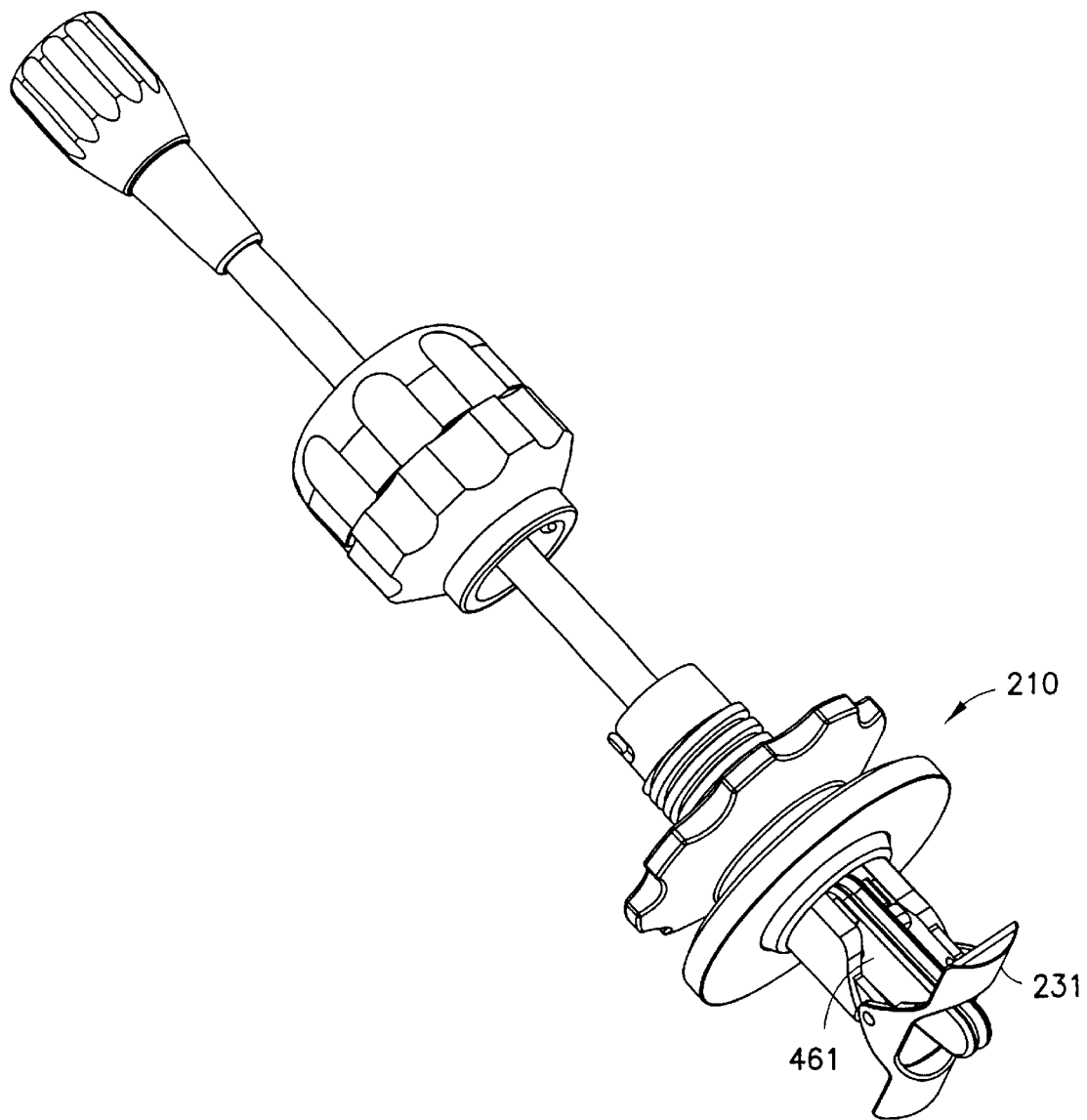
FIG. 22 is a perspective view of the heart stabilizer device, with the stabilizing assembly shown in a folded configuration and being inserted into the port device of the invention.
Figure 23:
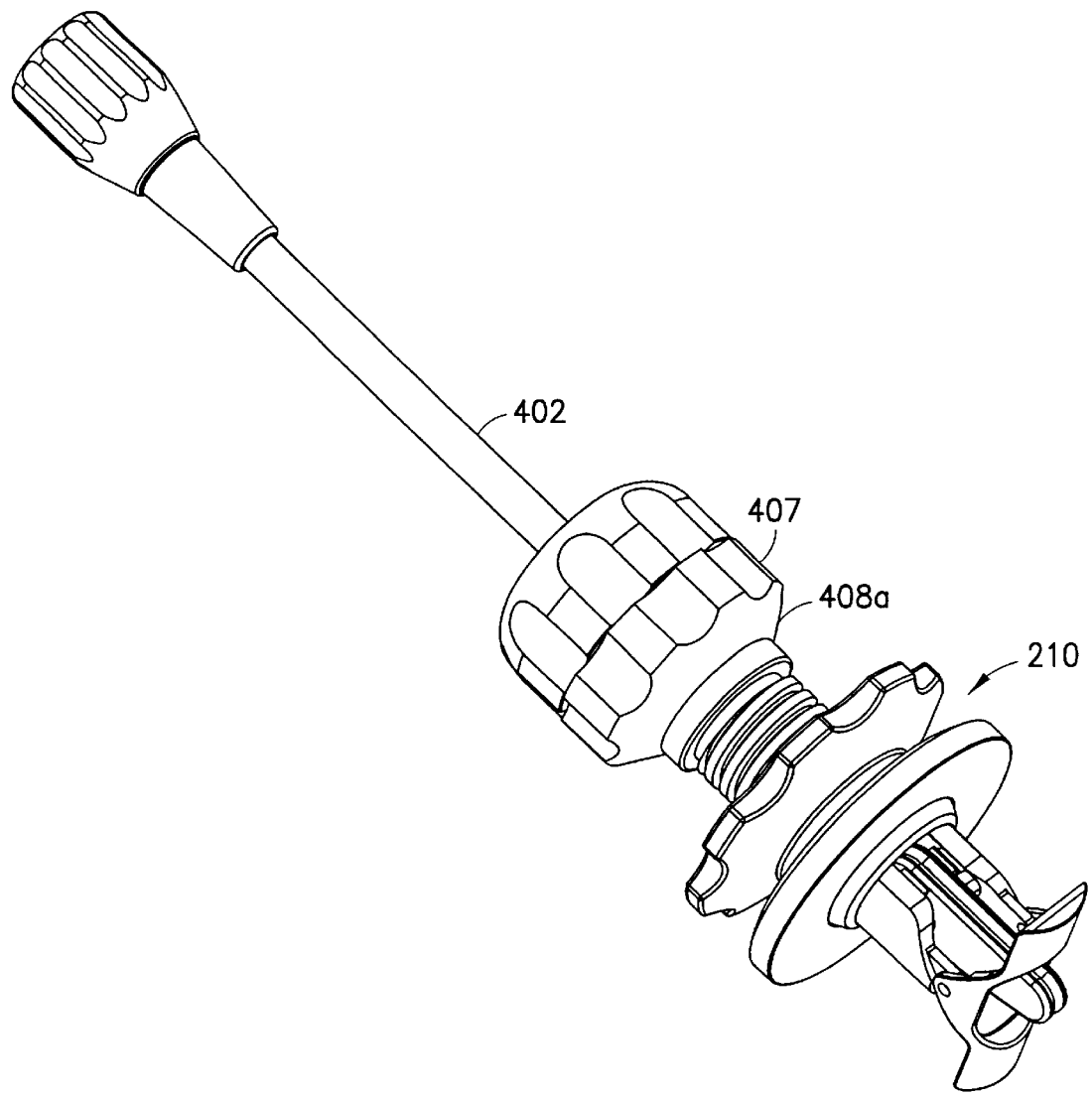
FIG. 23 is a perspective view of the heart stabilizer device, with the stabilizing assembly shown in a folded configuration and being inserted into the port device-of the invention and also with a shaft lock being coupled to the port device.
Figure 24:
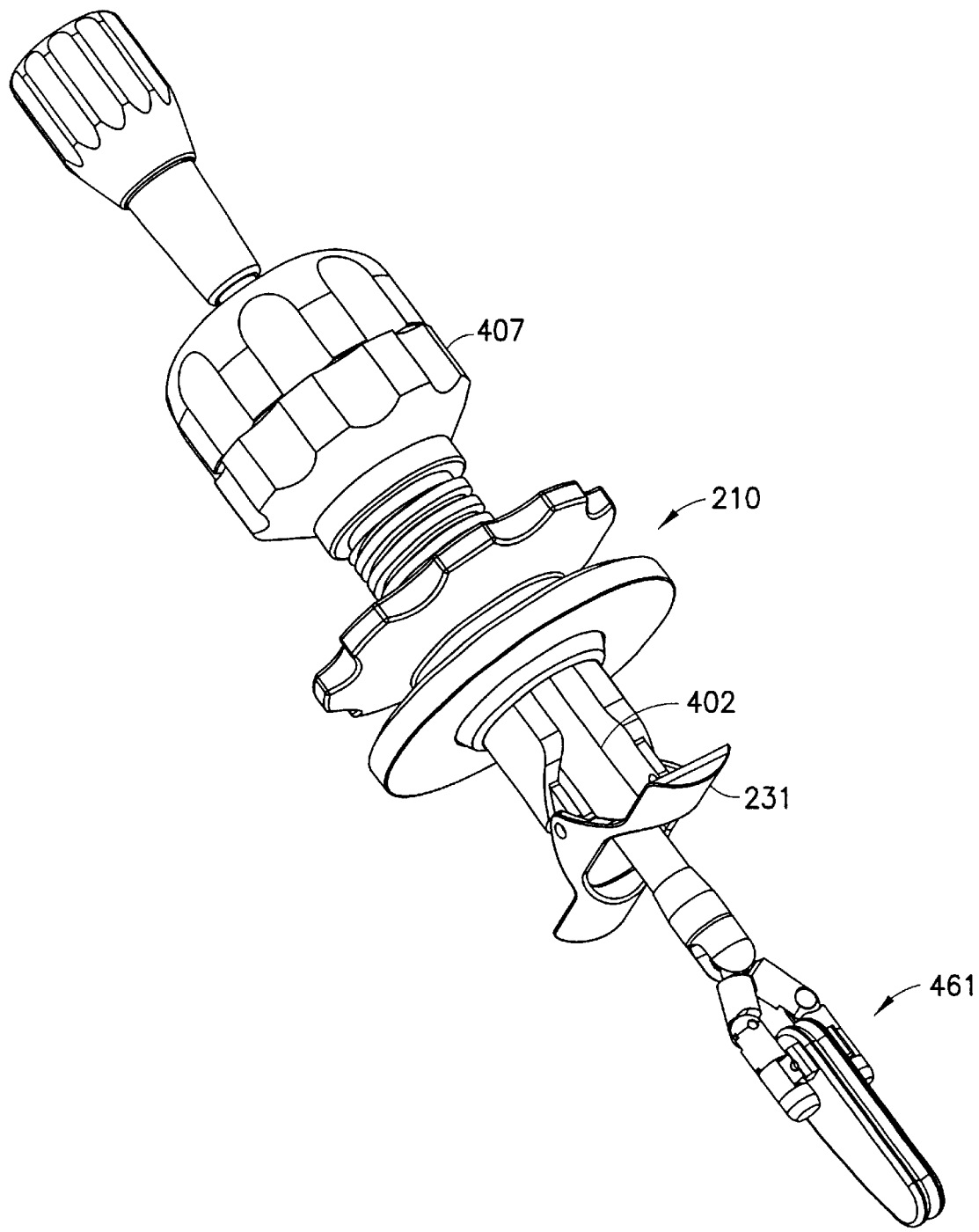
FIG. 24 is a perspective view of the heart stabilizer device, with the stabilizing assembly shown in a folded configuration and being extended through the port device of the invention.

The stabilizing assembly 461 is inserted into a port 210 (FIG. 22) which is mounted in a chest wall of a patient's body (not shown). The shaft lock 407, loosely provided about the shaft 402, is slid along the shaft 402 toward the port, and the port connector 408a of the shaft lock is then coupled to the port (FIG. 23). The shaft 402 is then moved through the shaft lock 407 until the stabilizing assembly 461 is moved beyond the swivel 231 of the port 210 to a location within the chest cavity permitting expansion of the stabilizing assembly 461 (FIG. 24). The shaft lock 407 is then tightened to retain the shaft 402 at the selected location relative to the port 210.

Figure 25:
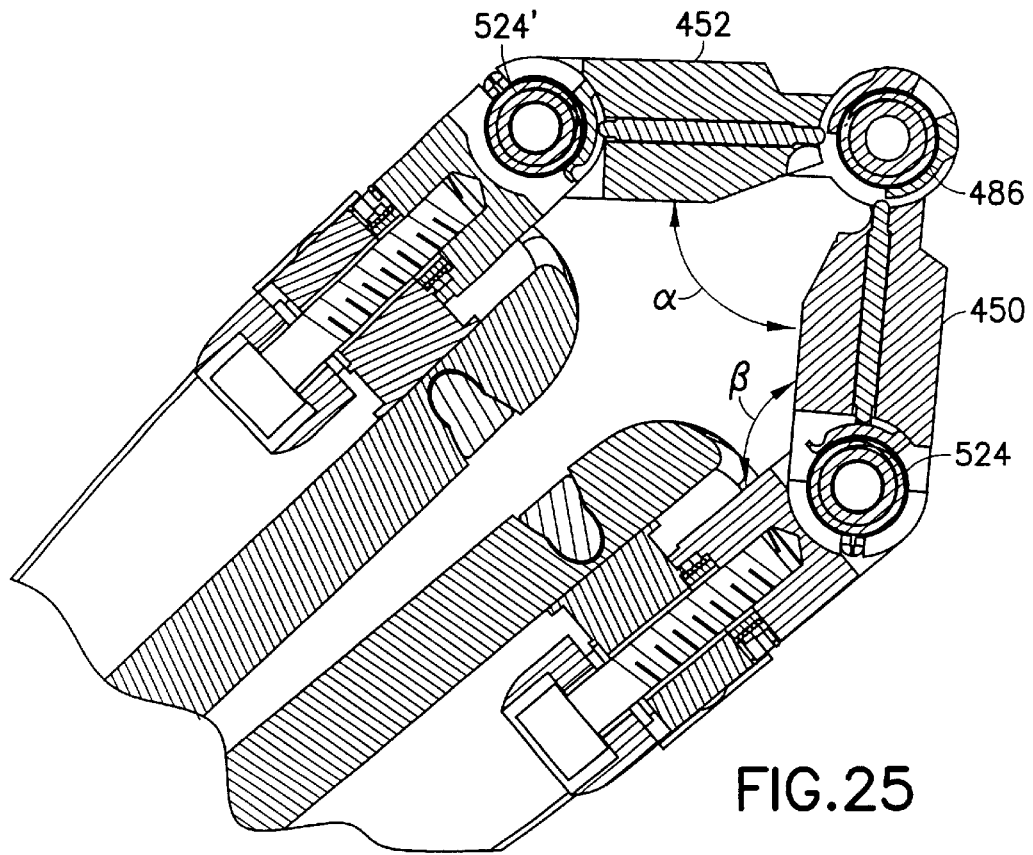
FIG. 25 is a partial longitudinal section view of the stabilizing assembly in a partially open first configuration.
Figure 26:
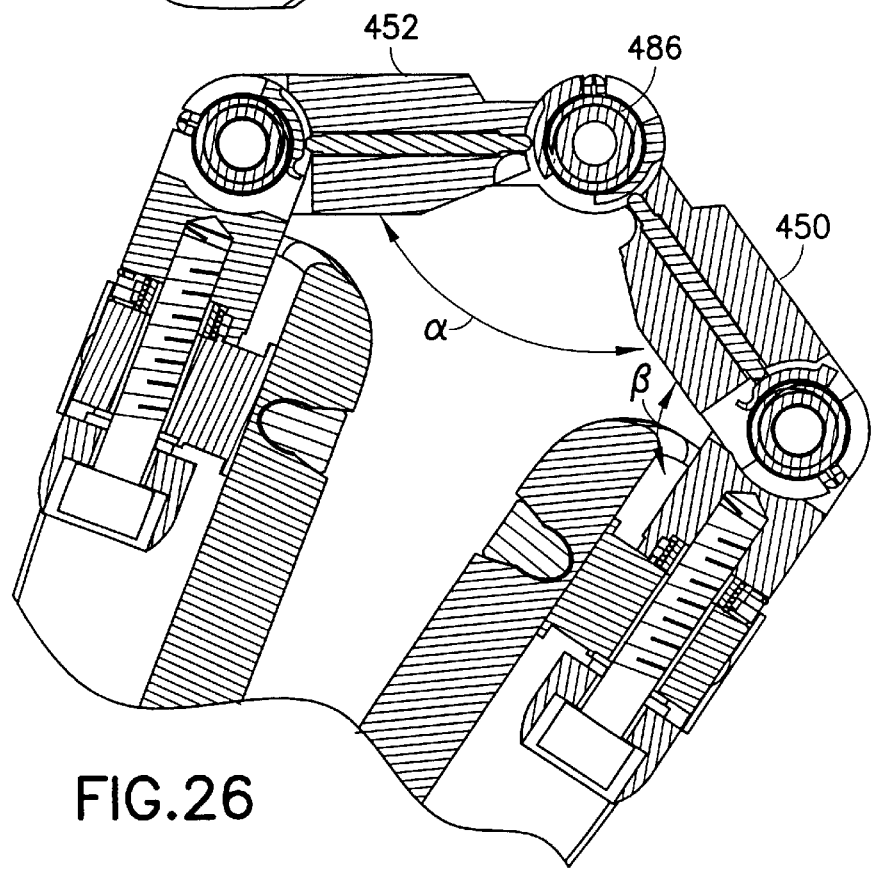
FIG. 26 is a partial longitudinal section view of the stabilizing assembly in a partially open second configuration more open that the first configuration.
Figure 27:
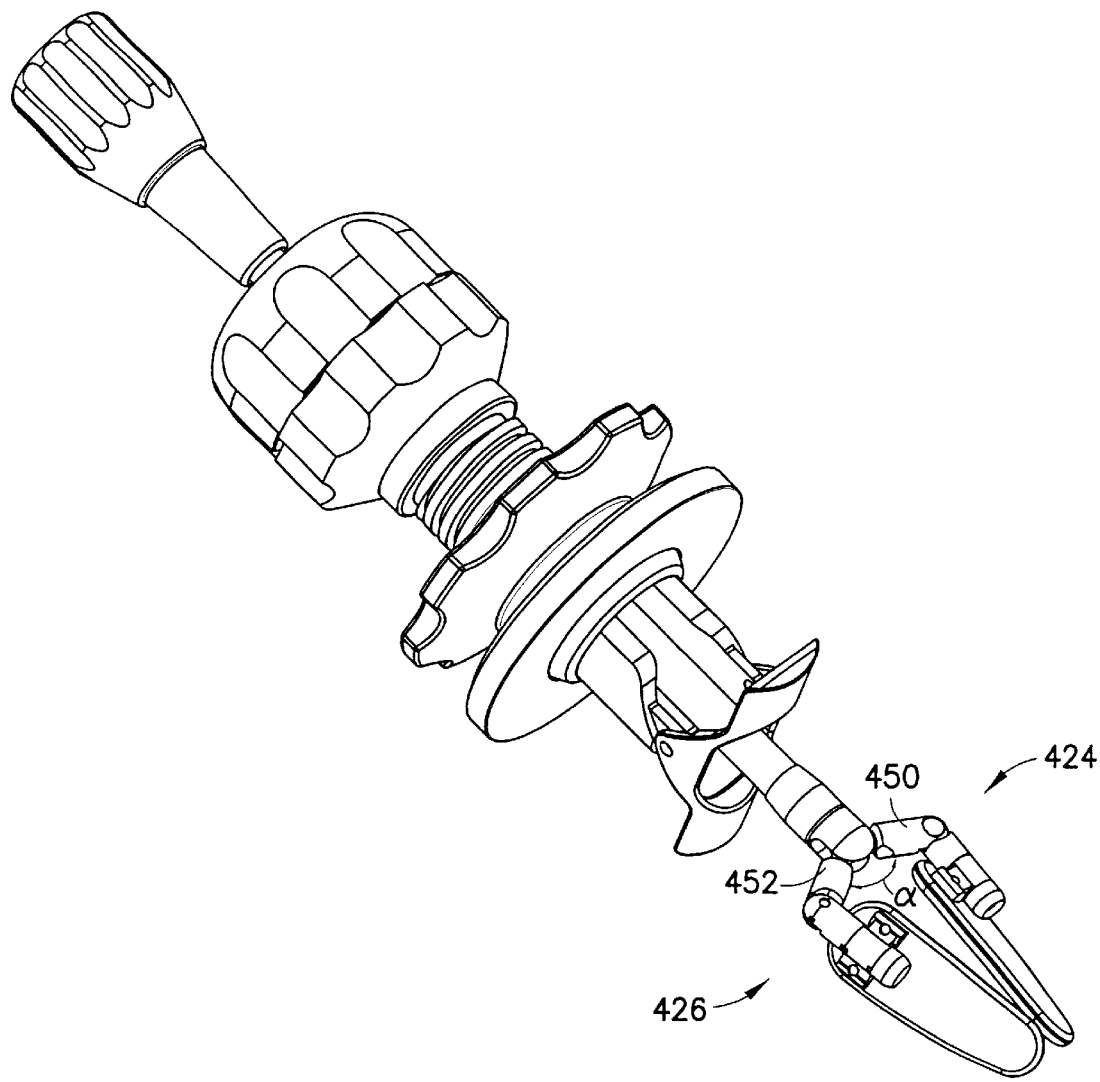
FIG. 27 is a perspective view of the heart stabilizer device, with the stabilizing assembly shown extended through the port device of the invention and in the second configuration.
Figure 28:
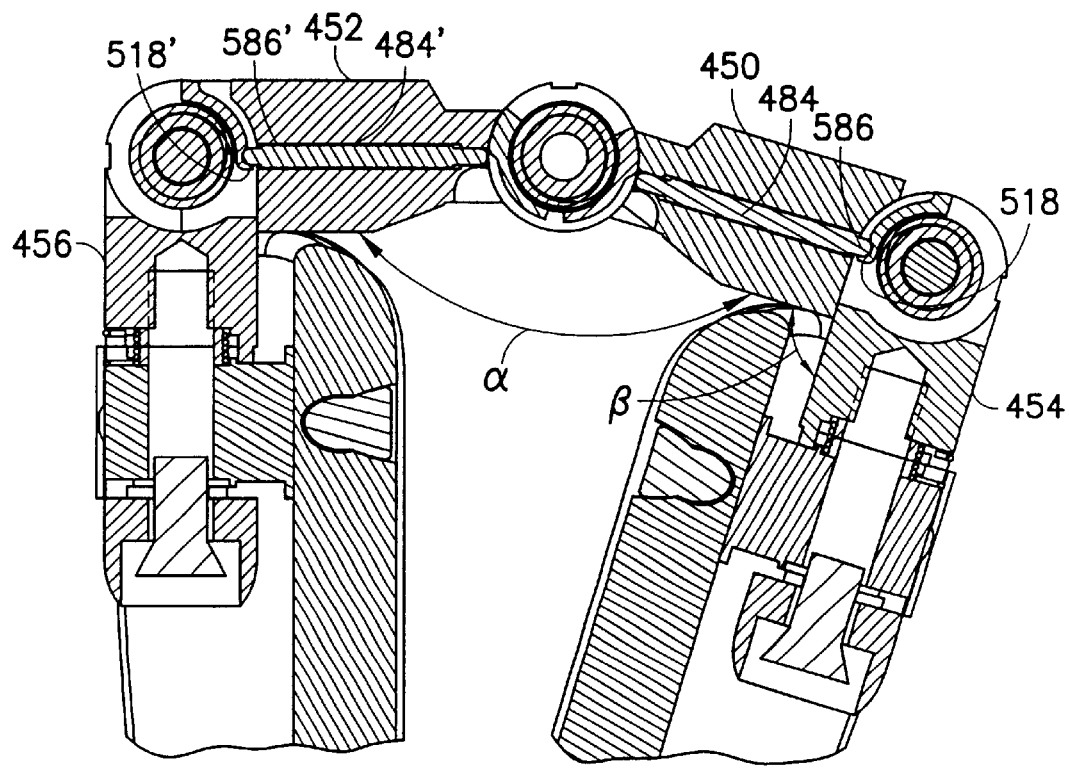
FIG. 28 is a partial longitudinal section view of the stabilizing assembly in a third configuration more open that the second configuration and in which the lock pins engage the lower arm cam locks.
Figure 29:
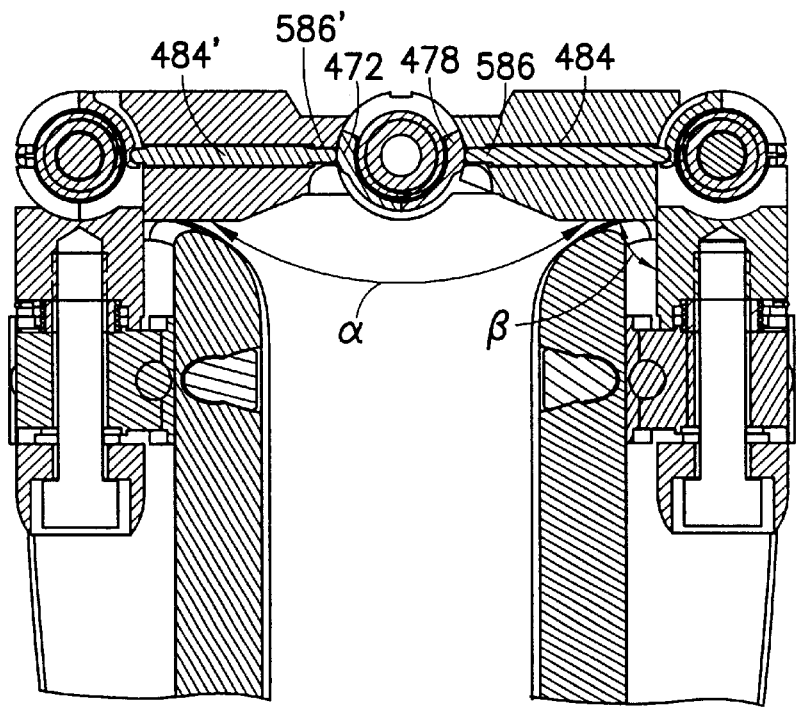
FIG. 29 is a partial longitudinal section view of the stabilizing assembly in a fully open fourth configuration in which the lower arms are locked relative to the upper arms.
Figure 30:
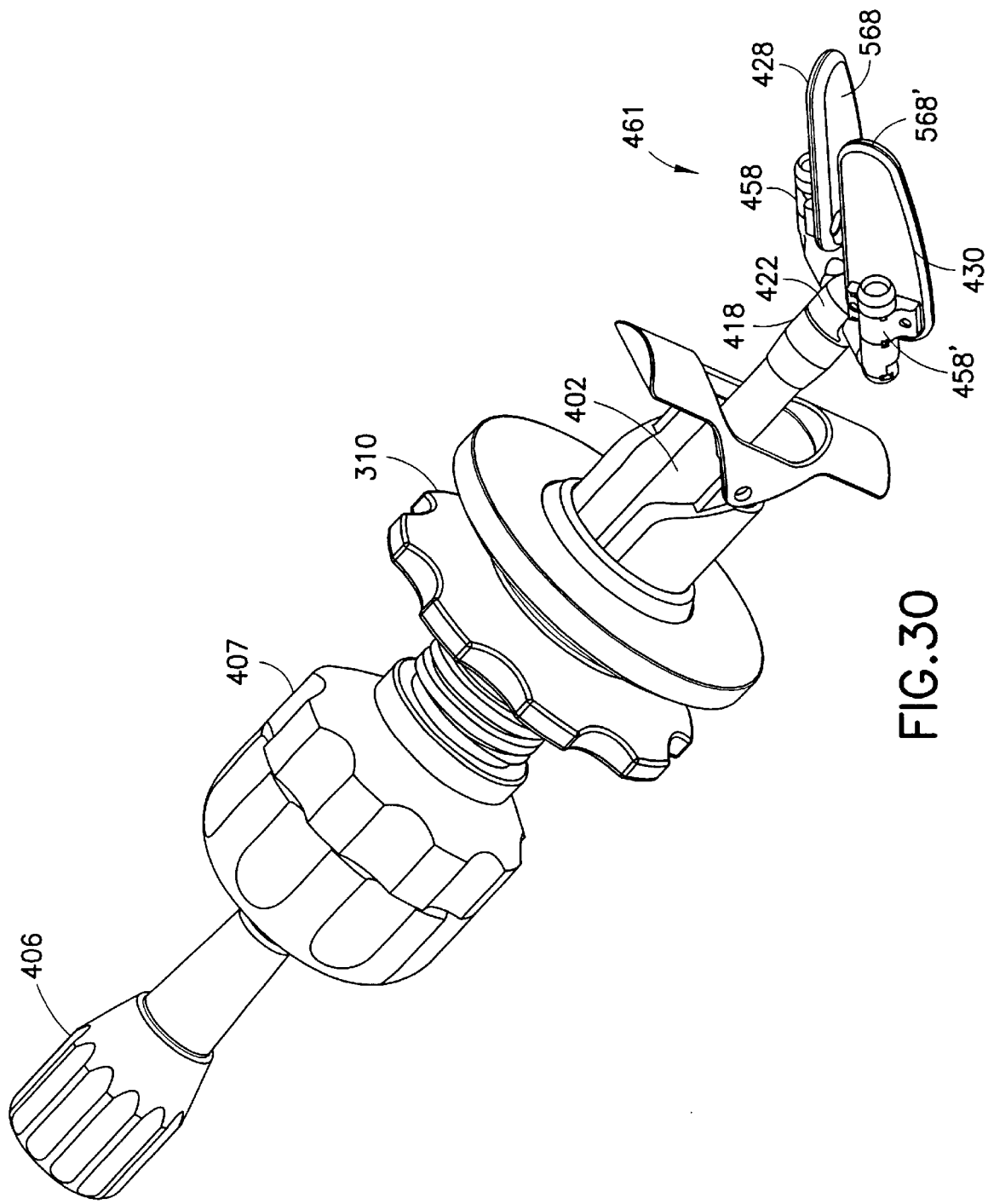
FIG. 30 is a perspective view of the heart stabilizer device, with the stabilizing assembly shown extended through the port device of the invention and in the fully open fourth configuration.

The knob 407 of the handle 406 is then operated to release the socket 422 from compression by the collar 418, thereby permitting movement of the articulating arms 424, 426 in accord with the forces of the springs and lock pins in the arms. More particularly, referring to FIGS. 20 and 25 through 27, when the socket is released, shoulder spring 487 operates to move the upper arms 450, 452 from a closed position ($\alpha$ equals approximately 47° in FIG. 20) toward a more open position ($\alpha$ equals approximately 87° in FIG. 25, and $\alpha$ equals approximately 126° in FIG. 26 and 27). In addition, elbow springs 524, 524' operate to bend the lower arms 454, 456 relative to the upper arms 450, 452 toward a smaller relative angle $\beta$. In FIG. 20, $\beta$ is approximately 156°; in FIG. 25, $\beta$ is approximately 135°; and in FIG. 26, $\beta$ is approximately 111°. Referring to FIG. 28, when $\alpha$ is approximately 163°, $\beta$ is substantially 90°, and the distal ends 586, 586' of the lock pins 484, 484' in the upper arms 450, 452 engage the cam locks 518, 518' of the elbows 510, 510' of the lower arms 454, 456. Then, as shown in FIG. 29, when the angle $\alpha$ is substantially 180°, the lock pins 484, 484' are engaged by the cams 472, 478 on the upper arms to lock the upper and lower arms at an angle $\beta$ of 90°. It is noted that $\beta$ is dependent on $\alpha$ only in that as $\alpha$ increases, so does $\beta$ as a result of the springs in the elbow joints. The only fixed relationship between $\alpha$ and $\beta$ are when the arms are fully folded, or fully deployed. It will be appreciated that this above described deployment and arm locking is automatic after the socket 436 is released from the collar 418. After deployment, the handle 406 may be operated to cause the collar to again clamp on the socket to prevent any relative movement of the upper arms which may otherwise potentially destabilize the stabilizer assembly 461.

Once the upper and lower arms are locked relative to each other, the shaft 402 (FIG. 16) may be unlocked from the shaft lock 407 and longitudinally moved such that the contact surfaces 568, 568' of the feet 428, 430 contact the heart wall. The feet are adapted to rotate at the wrist mounts 458, 460 relative to the lower arms to contour to the heart wall. The stops 546 on the lower arms (FIG. 19) preferably limit rotation of the feet to ninety-degrees relative to the orientation shown in FIG. 21. The shaft 402 is again locked within the shaft lock such that the feet apply sufficient pressure against the wall of the heart to effectively immobilize motion of the heart wall between the feet such that the bypass procedure may be performed between the feet.

Furthermore, after the POPCAB procedure, when it is desired to withdraw the heart stabilizer through the port, the handle 406 may be operated to unlock the stabilizer assembly 461. The shaft of the stabilizer is then released from the shaft lock and/or the port connector of the shaft lock is released from the port, and then the stabilizer assembly is forced proximally. When the upper arms contact the port, the upper arms are forced to fold in a reverse operation to deployment, i.e., to a smaller angle $\alpha$, and release the lock pins from the cams and cam locks. As the upper arms fold about the shoulder, the contact surfaces of the feet contact each other and rotate such that the contact surfaces are substantially coplanar. This, in turn, causes the lower arms to rotate about the elbow such that an increased angle $\beta$ is provided between the upper and lower arms permitting withdrawal of the assembly through the port.

According to various embodiments of the heart stabilizer, the feet of the stabilizer may be further adapted to facilitate immobilization of the heart wall between the feet. In addition to compressive forces, the feet may be adapted to apply suction, chemical agents, electrical current, or thermal cooling to enhance the heart wall immobilization.

There have been described and illustrated herein several embodiments of a system for performing POPCAB and a port device and heart stabilizer therefor. While particular embodiments of the invention have been described, it is not intended that the invention be limited thereto, as it is intended that the invention be as broad in scope as the art will allow and that the specification be read likewise. Thus, while the port device has been disclosed with various swivel elements, it will be appreciated that other swivel elements, and means for opening the swivel elements, including springs and mechanical systems may be used as well. In addition, while particular types of connecting means-for coupling devices, e.g., the introducer, the heart stabilizer, etc. to the port have been disclosed, it will be understood that other connecting means can be used. Also, while various means for orienting the port device relative to the heart wall have been disclosed, it will be appreciated that other such orienting means can be used was well. Furthermore, it will be appreciated that any one or more of the features of the individual port device embodiments may be incorporated into the other embodiments. Furthermore, with respect to the heart stabilizer, while various means for opening, and limiting the extent of opening, of the stabilizing assemblies has been disclosed, it will be appreciated that other means providing the same function may be used. Moreover, while particular preferred angles between the elements of the stabilizing assemblies have been disclosed, it will be appreciated that other preferred angles can be used, with angles other than those disclosed causing engagement of the cams to lock the arms. It will therefore be appreciated by those skilled in the art that yet other modifications could be made to the provided invention without deviating from its spirit and scope as claimed.

What is claimed is:

1. A heart stabilization device, comprising:
   a) a shaft having a proximal end and a distal end and defining a longitudinal axis; and
   b) a pair of stabilization pads each having a contact surface which is adapted to contact a surface of the heart, said pads being coupled to said distal end in a manner which permits one of said pads to rotate about a first axis and the other of said pads to rotate about a second axis substantially parallel to but not coaxial with said first axis,
   wherein said first axis extends substantially parallel to the contact surface of said one of said pads and said second axis extends substantially parallel to said contact surface of said other of said pads, and
   further wherein said pads are movable between a closed configuration in which said contact surfaces are in contact with each other, and an open configuration in which said contact surfaces are separated from each other.

2. A heart stabilization device, comprising:
   a) a shaft having a proximal end and a distal end and defining a longitudinal axis; and
   b) a pair of stabilization pads each having a contact surface which is adapted to contact a surface of the heart, said pads being coupled to said distal end in a manner which permits one of said pads to rotate about a first axis and the other of said pads to rotate about a second axis substantially parallel to but not coaxial with said first axis, wherein said pads are movable between a first orientation in which said pads extend in a first direction substantially parallel to said longitudinal axis and a second orientation in which said pads extend in a second direction substantially parallel to each other and obliquely relative to said longitudinal axis.

3. A heart stabilization device according to claim 2, further comprising:
   c) means for urging said pads into said second orientation.

4. A heart stabilization device, comprising:
   a) a shaft having a proximal end and a distal end and defining a longitudinal axis; and
   b) a pair of stabilization pads each having a contact surface which is adapted to contact a surface of the heart, said pads being coupled to said distal end in a manner which permits one of said pads to rotate about a first axis and the other of said pads to rotate about a second axis substantially parallel to but not coaxial with said first axis,
   wherein when said pads are in said first orientation, said contact surfaces are in contact with or adjacently facing each other.

5. A heart stabilization device, comprising:
   a) a shaft having a proximal end and a distal end and defining a longitudinal axis; and
   b) a pair of stabilization pads each having a contact surface which is adapted to contact a surface of the heart, said pads being coupled to said distal end in a manner which permits one of said pads to rotate about a first axis and the other of said pads to rotate about a second axis substantially parallel to but not coaxial with said first axis.
   wherein each of said pads is coupled to said distal end of said shaft with a multiple joint arm assembly.

6. A heart stabilization device according to claim 5, wherein:
   each said multiple joint arm assembly includes a shoulder joint, an elbow joint and a wrist joint.

7. A heart stabilization device according to claim 5, wherein:
   each joint of said multiple joint arm assembly includes a stop to limit the degree of rotation about each said joint.

8. A heart stabilization device according to claim 5, wherein:
   each joint of said multiple joint arm assembly includes a spring element which urges said joint into a predetermined configuration.

9. A heart stabilization device, comprising:
   a) an elongate shaft having a proximal end and a distal end and defining a longitudinal axis;
   b) first and second upper arm elements rotatably coupled with a first coupling to said distal end of said shaft;
   c) first and second lower arm elements rotatably coupled with first and second elbow joint couplings to said first and second upper arm elements, respectively;
   d) first and second pad supporting elements rotatably coupled with first and second wrist joint couplings to said first and second lower arm elements, respectively; and
   e) first and second stabilization pads mounted to said first and second pad supporting elements, respectively, each of said pads having a contact surface adapted to contact a surface of the heart.

10. A heart stabilization device according to claim 9, wherein:
    said first coupling includes a socket structure at said distal end of said shaft and a ball formed one half by each of said first and second upper arm elements, said upper arm elements permitted to rotate relative to each other.

11. A heart stabilization device according to claim 9, wherein:
    said first coupling, said first and second elbow joint couplings, and said first and second wrist joint couplings each include stops to limit a respective degree of rotation.

12. A heart stabilization device according to claim 9, wherein:
    said first coupling, said first and second elbow joint couplings, and said first and second wrist joint couplings each include spring elements to bias the respective elements coupled thereto into a predetermined configuration.

13. A heart stabilization device according to claim 9, wherein:
    said shaft includes means for locking said first coupling such that said upper arms are substantially fixed relative to said shaft.

14. A heart stabilization device, comprising:
    a) an elongate shaft having a proximal end and a distal end, said distal end defining a substantially spherical socket portion;
    b) a pair of stabilization pads each having a contact surface which is adapted to contact a surface of the heart; and
    c) a pair of arm assemblies coupling said pair of pads to said shaft, each of said arm assemblies including a proximal portion having a complementary substantially hemispherical shape, said proximal portions being provided in said socket portion such that said hemispherical proximal portions are each rotatable relative to the other within said socket portion.

15. A heart stabilization device according to claim 14, wherein:
    said hemispherical proximal portions are rotatable up to 180° relative to each other.

16. A heart stabilization device according to claim 14, further comprising:
    d) means for locking said hemispherical proximal portions relative to each other within said socket portion.

17. A heart stablization device, comprising:
    a) a shaft having a proximal end and a distal end;
    b) first and second articulating arms coupled to said distal end, each said articulating arm including an upper arm, a lower arm rotatable relative to said upper arm, and a wrist mount at a distal end of said lower arm and being rotatable about a longitudinal axis of said lower arm; and
    c) first and second feet, said first foot coupled to said wrist mount of said first articulating arm and said second foot coupled to said wrist mount of said second articulating arm.

18. A heart stabilization device according to claim 17, wherein:
    said first and second articulating arms include spring elements which rotate said lower arms relative to said upper arms.

19. A heart stabilization device according to claim 17, wherein:

said first and second articulating arms include spring elements which rotate said wrist mounts relative to said lower arms.

20. A heart stabilization device according to claim 17, wherein:

said first and second articulating arms include stop means for limiting the rotation of said lower arms relative to said upper arms.

21. A heart stabilization device according to claim 20, wherein:

said stop means includes a pin and a cam.

22. A heart stabilization device according to claim 17, further comprising:

d) a lock means for locking the relative position of said articulating arms.

23. A heart stabilization device according to claim 17, wherein:

said first and second articulating arms fold automatically when upper arms are forced distally.

24. A surgery system for performing heart surgery through a chest wall, comprising:

a) a port, including,
  i) a tubular body having a proximal portion and a distal portion,
  ii) at least one swivel rotatable about said distal portion of said body, said at least one swivel adapted to move between a first orientation in which said swivel extends in substantially a same direction as said body, and a second orientation at an angle relative to said first orientation, and
  iii) means for clamping the chest wall against said swivel, said means located about said-tubular body; and b) a heart stabilization device, including,
  i) a shaft having a proximal end and a distal end,
  ii) a shaft lock means for locking said shaft relative to said port device,
  iii) first and second articulating arms at said distal end of said shaft, each of said first and second articulating arms including a distal end, and
  iv) first and second feet at said respective distal ends of said arms.

25. A surgery system according to claim 24, wherein:

said tubular body includes a first coupling structure, and said shaft lock means includes a compressible element about said shaft and first and second clamping elements which cooperate to clamp and compress said compressible element, said shaft lock means including a second coupling structure which is couplable to said first coupling structure.

26. A surgery system according to claim 25, wherein:

said compressible element is substantially spherical and rotatable within said clamping elements such that when said clamping elements are loosened relative to each other, said shaft may be angularly positioned relative to said first and second clamping elements.

27. A surgery system according to claim 24, wherein:

said first and second articulating arms each include an upper arm, a lower arm rotatable relative to said upper arm, and a wrist mount at a distal end of said lower arm, said first and second feet coupled to respective wrist mounts on said respective arms.

28. A surgery system according to claim 27, wherein:

when said first and second articulating arms are located distally relative to said distal portion of said tubular body of said port device, said first and second articulating arms automatically fold when said shaft is moved to force said articulating arms are moved proximally relative to said port device.

29. A surgery system according to claim 28, wherein:

when said arms automatically fold, said feet rotate toward each other.

30. A surgery system according to claim 27, wherein:

said articulating arms are adapted to expand to a size greater than a diameter of said port and be folded to a size smaller than said diameter of said port.

31. A surgery system according to claim 30, wherein:

said articulating arms are adapted to automatically expand.

32. A surgery system according to claim 30, wherein:

said articulating arms may be locked in an expanded or a folded configuration.

* * * * *